(12) United States Patent
Dani et al.

(10) Patent No.: US 12,246,188 B2
(45) Date of Patent: *Mar. 11, 2025

(54) SELECTION OF PROBABILITY THRESHOLDS FOR GENERATING CARDIAC ARRHYTHMIA NOTIFICATIONS

(71) Applicant: Medtronic, Inc., Minneapolis, MN (US)

(72) Inventors: Siddharth Dani, Minneapolis, MN (US); Tarek D. Haddad, Minneapolis, MN (US); Donald R. Musgrove, Minneapolis, MN (US); Andrew Radtke, Minneapolis, MN (US); Niranjan Chakravarthy, Singapore (SG); Rodolphe Katra, Blaine, MN (US); Lindsay A. Pedalty, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 41 days.

This patent is subject to a terminal disclaimer.

(21) Appl. No.: 18/155,803

(22) Filed: Jan. 18, 2023

(65) Prior Publication Data

US 2023/0149726 A1 May 18, 2023

Related U.S. Application Data

(63) Continuation of application No. 16/850,833, filed on Apr. 16, 2020, now Pat. No. 11,583,687.

(Continued)

(51) Int. Cl.
*A61N 1/39* (2006.01)
*A61N 1/365* (2006.01)
(Continued)

(52) U.S. Cl.
CPC ....... *A61N 1/3956* (2013.01); *A61N 1/36592* (2013.01); *G16H 10/60* (2018.01);
(Continued)

(58) Field of Classification Search
CPC ...................................................... A61N 1/39
See application file for complete search history.

(56) References Cited

U.S. PATENT DOCUMENTS 4,458,691 A 7/1984 Netravali
6,212,428 B1 4/2001 Hsu et al.
(Continued)

FOREIGN PATENT DOCUMENTS

CN 106572807 A 4/2017
CN 106573149 A 4/2017
(Continued)

OTHER PUBLICATIONS

"Classify ECG Signals Using Long Short-Term Memory Networks," MATLAB, retrieved from https://www.mathworks.com/help/signal/examples/classify-ecg-signals-using-long-short-term-Memory-networks.html, Nov. 2, 2018, 19 pp.

(Continued)

*Primary Examiner* — Di Xiao
(74) *Attorney, Agent, or Firm* — Shumaker & Sieffert, P.A.

(57) ABSTRACT

Techniques are disclosed for monitoring a patient for the occurrence of a cardiac arrhythmia. A computing system generates sample probability values by applying a machine learning model to sample patient data. The machine learning model determines a respective probability value that indicates a probability that the cardiac arrhythmia occurred during each respective temporal window. The computing system outputs a user interface comprising graphical data based on the sample probability values and receives, via the (Continued)

user interface, an indication of user input to select a probability threshold for a patient. The computing system receives patient data for the patient and applies the machine learning model to the patient data to determine a current probability value. In response to the determination that the current probability exceeds the probability threshold for the patient, the computing system generates an alert indicating the patient has likely experienced the occurrence of the cardiac arrhythmia.

18 Claims, 10 Drawing Sheets

Related U.S. Application Data

(60) Provisional application No. 62/843,707, filed on May 6, 2019.

(51) Int. Cl.
  *G16H 10/60* (2018.01)
  *G16H 40/63* (2018.01)
  *G16H 50/20* (2018.01)
  *G16H 50/50* (2018.01)

(52) U.S. Cl.
  CPC ............. *G16H 40/63* (2018.01); *G16H 50/20* (2018.01); *G16H 50/50* (2018.01)

(56) References Cited

U.S. PATENT DOCUMENTS

| | | | |
|---|---|---|---|
| 6,308,094 B1 | 10/2001 | Shusterman et al. |
| 6,594,523 B1 | 7/2003 | Levine |
| 8,103,346 B2 | 1/2012 | Mass et al. |
| 8,521,281 B2 | 8/2013 | Patel et al. |
| 9,149,637 B2 | 10/2015 | Warren et al. |
| 9,183,351 B2 | 11/2015 | Shusterman |
| 9,483,529 B1 | 11/2016 | Pasoi et al. |
| 9,585,590 B2 | 3/2017 | McNair |
| 9,743,890 B2 | 8/2017 | Lord et al. |
| 9,775,559 B2 | 10/2017 | Zhang et al. |
| 10,368,746 B2 | 8/2019 | Huelskamp et al. |
| 10,463,269 B2 | 11/2019 | Boleyn et al. |
| 10,744,334 B2 | 8/2020 | Perschbacher et al. |
| 10,888,282 B2 | 1/2021 | Ong et al. |
| 11,311,230 B2 | 4/2022 | Sullivan et al. |
| 11,355,244 B2 | 6/2022 | Haddad et al. |
| 11,443,852 B2 | 9/2022 | Chakravarthy et al. |
| 11,723,577 B2 | 8/2023 | Pedalty et al. |
| 2002/0016550 A1 | 2/2002 | Sweeney et al. |
| 2002/0123768 A1 | 9/2002 | Gilkerson et al. |
| 2006/0247709 A1 | 11/2006 | Gottesman et al. |
| 2009/0259269 A1 | 10/2009 | Brown |
| 2010/0179444 A1 | 7/2010 | O'Brien et al. |
| 2010/0217141 A1 | 8/2010 | Ostrow |
| 2010/0268103 A1 | 10/2010 | McNamara et al. |
| 2010/0280841 A1 | 11/2010 | Dong et al. |
| 2010/0312130 A1 | 12/2010 | Zhang et al. |
| 2010/0312131 A1 | 12/2010 | Naware et al. |
| 2011/0270109 A1 | 11/2011 | Zhang et al. |
| 2012/0004563 A1 | 1/2012 | Kim et al. |
| 2012/0209126 A1 | 8/2012 | Amos et al. |
| 2013/0231947 A1 | 9/2013 | Shusterman |
| 2013/0274524 A1 | 10/2013 | Dakka et al. |
| 2013/0274624 A1 | 10/2013 | Mahajan et al. |
| 2014/0142448 A1 | 5/2014 | Bae et al. |
| 2014/0257063 A1 | 9/2014 | Ong et al. |
| 2014/0378856 A1 | 12/2014 | Koike et al. |
| 2015/0065894 A1 | 3/2015 | Airaksinen et al. |
| 2015/0164349 A1 | 6/2015 | Gopalakrishnan et al. |
| 2015/0216435 A1 | 8/2015 | Bokan et al. |
| 2015/0265217 A1 | 9/2015 | Penders et al. |
| 2016/0008615 A1 | 1/2016 | Stahmann et al. |
| 2016/0022164 A1 | 1/2016 | Brockway et al. |
| 2016/0022166 A1 | 1/2016 | Stadler |
| 2016/0135706 A1 | 5/2016 | Sullivan et al. |
| 2016/0192853 A1 | 7/2016 | Bardy et al. |
| 2016/0220137 A1 | 8/2016 | Mahajan et al. |
| 2016/0232280 A1 | 8/2016 | Apte et al. |
| 2017/0095673 A1 | 4/2017 | Ludwig et al. |
| 2017/0105683 A1 | 4/2017 | Xue |
| 2017/0156592 A1 | 6/2017 | Fu |
| 2017/0196458 A1 | 7/2017 | Ternes et al. |
| 2017/0265765 A1 | 9/2017 | Baumann et al. |
| 2017/0290550 A1 | 10/2017 | Perschbacher et al. |
| 2017/0347894 A1 | 12/2017 | Bhushan et al. |
| 2017/0354365 A1 | 12/2017 | Zhou |
| 2018/0008976 A1 | 3/2018 | Okazaki |
| 2018/0089763 A1 | 3/2018 | Okazaki |
| 2018/0146874 A1 | 5/2018 | Walker et al. |
| 2018/0146929 A1 | 5/2018 | Joo et al. |
| 2018/0206721 A1* | 7/2018 | Zhang .................... A61B 5/363 |
| 2018/0233227 A1 | 8/2018 | Galloway et al. |
| 2018/0272147 A1 | 9/2018 | Freeman et al. |
| 2018/0279891 A1 | 10/2018 | Miao et al. |
| 2018/0310892 A1 | 11/2018 | Perschbacher et al. |
| 2019/0008461 A1 | 1/2019 | Gupta et al. |
| 2019/0029552 A1 | 1/2019 | Perschbacher et al. |
| 2019/0038148 A1 | 2/2019 | Valys et al. |
| 2019/0038149 A1 | 2/2019 | Gopalakrishnan et al. |
| 2019/0090774 A1 | 3/2019 | Yang et al. |
| 2019/0122097 A1 | 4/2019 | Shibahara et al. |
| 2019/0130554 A1 | 5/2019 | Rothberg et al. |
| 2019/0209022 A1 | 7/2019 | Sobol et al. |
| 2019/0216350 A1 | 7/2019 | Sullivan et al. |
| 2019/0231207 A1 | 8/2019 | Perschbacher et al. |
| 2019/0272920 A1 | 9/2019 | Teplitzky |
| 2019/0275335 A1 | 9/2019 | Volpe et al. |
| 2019/0328251 A1 | 10/2019 | Jin |
| 2019/0343415 A1* | 11/2019 | Saha ...................... G16H 50/20 |
| 2019/0365342 A1 | 12/2019 | Ghaffarzadegan et al. |
| 2019/0378620 A1 | 12/2019 | Saren |
| 2020/0100693 A1 | 4/2020 | Velo |
| 2020/0108260 A1 | 4/2020 | Haddad et al. |
| 2020/0178825 A1 | 6/2020 | Weijia et al. |
| 2020/0288997 A1 | 9/2020 | Shute et al. |
| 2020/0352462 A1 | 11/2020 | Pedalty et al. |
| 2020/0352466 A1 | 11/2020 | Chakravarthy et al. |
| 2020/0352521 A1 | 11/2020 | Chakravarthy et al. |
| 2020/0353271 A1 | 11/2020 | Dani et al. |
| 2020/0357517 A1 | 11/2020 | Haddad et al. |
| 2020/0357518 A1 | 11/2020 | Musgrove et al. |
| 2020/0357519 A1 | 11/2020 | Chakravarthy et al. |
| 2021/0137384 A1 | 5/2021 | Robinson et al. |
| 2021/0169736 A1 | 6/2021 | Wijshoff et al. |
| 2021/0204858 A1 | 7/2021 | Attia et al. |
| 2021/0338134 A1 | 11/2021 | Chakravarthy et al. |
| 2021/0338138 A1 | 11/2021 | Pedalty et al. |
| 2021/0343416 A1 | 11/2021 | Chakravarthy et al. |
| 2021/0345865 A1 | 11/2021 | Spillinger et al. |
| 2021/0358631 A1 | 11/2021 | Haddad et al. |
| 2023/0329624 A1 | 10/2023 | Pedalty et al. |

FOREIGN PATENT DOCUMENTS

| | | |
|---|---|---|
| CN | 106725428 A | 5/2017 |
| CN | 107408144 A | 11/2017 |
| CN | 107822622 A | 3/2018 |
| CN | 108030488 A | 5/2018 |
| CN | 108577823 A | 9/2018 |
| EP | 1218060 B1 | 8/2004 |
| EP | 2427105 A1 | 3/2012 |
| JP | 2013524865 A | 6/2013 |
| JP | 2012532633 A | 7/2013 |
| JP | 2014100473 A | 6/2014 |
| JP | 2018503885 A | 2/2018 |
| WO | 0124876 A1 | 4/2001 |
| WO | 2010129447 A1 | 11/2010 |
| WO | 2011008550 A1 | 1/2011 |
| WO | 2013/160538 A1 | 10/2013 |
| WO | 2015200527 A1 | 12/2015 |
| WO | 2017072250 A1 | 5/2017 |

(56) References Cited

FOREIGN PATENT DOCUMENTS

| WO | 2017091736 A1 | 6/2017 |
|---|---|---|
| WO | 2018119316 A1 | 6/2018 |
| WO | 2018162901 A1 | 9/2018 |
| WO | 2019075035 A1 | 4/2019 |
| WO | 2020049267 A1 | 3/2020 |

OTHER PUBLICATIONS

"Visualize Features of a Convolutional Neural Network," MATLAB & Simulink, Mar. 15, 2018, 9 pp.
"Visualize Features of a Convolutional Neural Network," MATLAB & Simulink, retrieved from https://www.mathworks.com/help/deeplearning/examples/visualize-features-of-a-convolutional-neural-network.html, Sep. 11, 2019, 7 pp.
Andersen et al., "A Deep Learning Approach for Real-Time Detection of Atrial Fibrillation," Expert Systems with Applications, vol. 114, Aug. 14, 2018, pp. 465-473.
Anonymous, "Receiver Operating Characteristic-Wikipedia," Mar. 20, 2019, Retrieved from the Internet: URL:https://en.wikipedia.org/w/index.php?title=Receiver_operating_characteristic&oldis-888671034#History, 12 pp.
Arrobo et al., "An Innovative Wireless Cardiac Rhythm Management (iCRM) System," Computer Science, 2014 Wireless Telecommunications Symposium, Jun. 2014, 5 pp.
Bresnick, "Machine Learning Algorithm Outperforms Cardiologists Reading EKGs", Health IT Analytics, Jul. 12, 2017, 5 pp.
Chen et al., "Electrocardiogram Recognition Based on Variational AutoEncoder," Machine Learning and Biometrics, IntechOpen, Aug. 29, 2018, pp. 71-90.
Fawaz et al., "Deep learning for time series classification: a review," Irirmas, Universite Haute Alsace, Dec. 7, 2018, 53 pp.
Habibzadeh et al., "On Determining the Most Appropriate Test Cut-Off Value: the Case of Tests with Continuous Results," Biochemia Medica, Oct. 15, 2016, pp. 297-307.
Isin et al., "Cardiac Arrhythmia Detection Using Deep Learning," Procedia Computer Science vol. 120, 2017 (Applicant points out, in accordance with MPEP 609.04(a), that the year of publication, 2017, is sufficiently earlier than the effective U.S. filing date, so that the particular month of publication is not in issue.) pp. 268-275.
Kelwade et al., "Prediction of Cardiac Arrhythmia using Artificial Neural Network," International Journal of Computer Applications (0975-8887), vol. 115—No. 20, Apr. 2015, 6 pp.
Lau et al., "Connecting the Dots: From Big Data to Healthy Heart," Circulation, vol. 134, No. 5, Aug. 2, 2017, 5 pp.
Madani et al., "Fast and Accurate View Classification of Echocardiograms Using Deep Learning," Nature Partner Journals, vol. 1, No. 6, Mar. 21, 2018, 8 pp.
Schirrmeister et al., "Deep Learning with Convolutional Neural Networks for Brain Mapping and Decoding of Movement-Related Information from the Human EEG," Cornell University Library, Mar. 16, 2017, 58 pp.
Schwab et al., "Beat by Beat: Classifying Cardiac Arrhythmias with Recurrent Neural Networks," 2017 Computing in Cardiology (CinC), vol. 44, Oct. 24, 2017, 4 pp.
Swerdlow et al., "An Innovative Wireless Cardiac Rhythm Management (iCRM) System," Advances in Arrhythmia and Electrophysiology, vol. 7, No. 6, Dec. 2014, pp. 1237-1261.
Swerdlow et al., "Troubleshooting Implanted Cardioverter Defibrillator Sensing Problems I," Advances in Arrhythmia and Electrophysiology, vol. 7, No. 6, Dec. 2014, pp. 1237-1261.
Wartzek et al., "ECG on the Road: Robust and Unobtrusive Estimation of Heart Rate," IEEE Transactions on Biomedical Engineering, vol. 58, No. 11, Nov. 2011, pp. 3112-3120.
Witten et al., "Data mining: Practical Machine Learning Tools and Techniques," Third Edition, Morgan Kaufmann, Feb. 3, 2011, 665 pp.
Prosecution History from U.S. Appl. No. 16/832,732, dated Mar. 2, 2022 through Jan. 13, 2023, 91 pp.
Prosecution History from U.S. Appl. No. 16/845,996, dated Aug. 16, 2022 through Jan. 9, 2023, 68 pp.
Prosecution History from U.S. Appl. No. 16/850,833 dated Jun. 23, 2022 through Oct. 19, 2022, 53 pp.
Prosecution History from U.S. Appl. No. 17/389,831, now issued U.S. Pat. No. 11,355,244, dated Sep. 10, 2021 through Apr. 25, 2022, 56 pp.
Response to Final Office Action dated Aug. 31, 2023 from U.S. Appl. No. 16/832,732, filed Nov. 27, 2023, 19 pp.
U.S. Appl. No. 18/479,228, filed Oct. 2, 2023, naming inventors Haddad et al.
Response to Office Action dated Jan. 9, 2023 from U.S. Appl. No. 16/845,996, filed Apr. 10, 2023, 11 pgs.
Response to Office Action dated Jan. 13, 2023 from U.S. Appl. No. 16/832,732, filed Apr. 12, 2023, 19 pp.
Advisory Action from U.S. Appl. No. 16/832,732 dated Dec. 14, 2023, 3 pp.
Office Action from U.S. Appl. No. 16/832,732 dated Mar. 14, 2024, 14 pp.
Final Office Action from U.S. Appl. No. 16/832,732 dated Aug. 31, 2023, 18 pp.
U.S. Appl. No. 18/309,309, filed Apr. 28, 2023, naming inventors Haddad et al.
U.S. Appl. No. 18/320,522, filed May 19, 2023, naming inventors Chakravarthy et al.
U.S. Appl. No. 18/331,756, filed Jun. 8, 2023, naming inventors Chakravarthy et al.
Hao et al., "Application of implantable cardioverter-defibrillator in patients with tachyventricular fatal arhythmias", vol. 26, No. 23, The Journal of Practical Medicine, Dec. 10, 2010, 4 pp., Translation provided for only the Abstract.
Corrected Notice of Allowance from U.S. Appl. No. 16/845,996 dated Jun. 2, 2023, 2 pp.
Notice of Allowability from U.S. Appl. No. 16/845,996 dated May 23, 2023, 10 pp.
Final Office Action from U.S. Appl. No. 16/832,732 dated Jul. 5, 2024, 13 pp.
Office Action from U.S. Appl. No. 18/479,228 dated Jun. 20, 2024, 20 pp.
Response to Office Action dated Mar. 14, 2024 from U.S. Appl. No. 16/832,732, filed May 20, 2024, 17 pp.
Advisory Action from U.S. Appl. No. 16/832,732 dated Sep. 9, 2024, 3 pp.
Response to Final Office Action dated Jul. 5, 2024 from U.S. Appl. No. 16/832,732, filed Aug. 29, 2024, 18 pp.
Response to Office Action dated Jun. 20, 2024 from U.S. Appl. No. 18/479,228, filed Sep. 19, 2024, 8 pp.
Response to Office Action dated Nov. 7, 2024 from U.S. Appl. No. 16/832,732, filed Jan. 27, 2025, 15 pp.

* cited by examiner

SELECTION OF PROBABILITY THRESHOLDS FOR GENERATING CARDIAC ARRHYTHMIA NOTIFICATIONS This application is a continuation of U.S. patent application Ser. No. 16/850,833, filed Apr. 16, 2020, which claims the benefit of U.S. Provisional Patent Application 62/843,707, filed May 6, 2019. The entire content of U.S. patent application Ser. No. 16/850,833 and U.S. Provisional Patent Application 62/843,707 are incorporated herein by reference.

FIELD

This disclosure generally relates to health monitoring and, more particularly, to monitoring cardiac health.

BACKGROUND

Malignant tachyarrhythmia, for example, ventricular fibrillation, is an uncoordinated contraction of the cardiac muscle of the ventricles in the heart and is the most commonly identified arrhythmia in cardiac arrest patients. If this arrhythmia continues for more than a few seconds, it may result in cardiogenic shock and cessation of effective blood circulation. Consequently, sudden cardiac death (SCD) may result in a matter of minutes.

In patients with a high risk of ventricular fibrillation, the use of an implantable medical device (IMD), such as an implantable cardioverter defibrillator (ICD), has been shown to be beneficial at preventing SCD. An ICD is a battery-powered electrical shock device, that may include an electrical housing electrode (sometimes referred to as a can electrode), that is typically coupled to one or more electrical lead wires placed within the heart. If an arrhythmia is sensed, the ICD may send a pulse via the electrical lead wires to shock the heart and restore its normal rhythm. Some ICDs have been configured to attempt to terminate detected tachyarrhythmias by delivery of anti-tachycardia pacing (ATP) prior to delivery of a shock. Additionally, ICDs have been configured to deliver relatively high magnitude post-shock pacing after successful termination of a tachyarrhythmia with a shock, in order to support the heart as it recovers from the shock. Some ICDs also deliver bradycardia pacing, cardiac resynchronization therapy (CRT), or other forms of pacing.

Other types of medical devices may be used for diagnostic purposes. For instance, an implanted or non-implanted medical device may monitor a patient's heart. A user, such as a physician, may review data generated by the medical device for occurrences of cardiac arrhythmias, e.g., atrial or ventricular tachyarrhythmia, or asystole. The user may diagnose a medical condition of the patient based on the identified occurrences of the cardiac arrhythmias.

SUMMARY

In general, the disclosure describes techniques for monitoring a patient for occurrences of cardiac arrhythmias. A computing system generates sample probability values by applying a machine learning model to sample patient data. In some examples, the computing system is a cloud computing system. The machine learning model determines a respective probability value that indicates a probability that a cardiac arrhythmia occurred during each respective temporal window. The computing system outputs a user interface comprising graphical data based on the sample probability values and receives, via the user interface, an indication of user input to select a probability threshold for a patient. The computing system receives patient data for the patient and applies the machine learning model to the patient data to determine a current probability value. In response to the determination that the current probability exceeds the probability threshold for the patient, the computing system generates a notification indicating the patient has likely experienced the cardiac arrhythmia. In this way, a user may use the user interface to efficiently configure the computing system with respect to the sensitivity and specificity of the computing system.

In one aspect, this disclosure describes a method comprising: generating, by a computing system that comprises processing circuitry and a storage medium, a set of sample probability values by applying a machine learning model to a sample set of patient data, wherein: the machine learning model is trained using patient data for a plurality of patients, the sample set comprises a plurality of temporal windows, and for each respective temporal window of the plurality of temporal windows, the machine learning model is configured to determine a respective probability value in the set of sample probability values that indicates a probability that a cardiac arrhythmia occurred during the respective temporal window; generating, by the computing system, graphical data based on the sample probability values; outputting, by the computing system, a user interface for display on a display device, the user interface comprising the graphical data; receiving, by the computing system, via the user interface, an indication of user input to select a probability threshold for a patient; receiving, by the computing system, patient data for the patient, wherein the patient data is collected by one or more medical devices; applying, by the computing system, the machine learning model to the patient data to determine a current probability value that indicates a probability that the patient has experienced an occurrence of a cardiac arrhythmia; determining, by the computing system, that the current probability value exceeds the probability threshold for the patient; and in response to determining that the current probability value is greater than or equal to the probability threshold for the patient, generating, by the computing system, a notification indicating that the patient has likely experienced the occurrence of the cardiac arrhythmia.

In another aspect, this disclosure describes a computing system comprising one or more processing circuits; and a storage medium storing instructions that, when executed, configure the one or more processing circuits to: generate a set of sample probability values by applying a machine learning model to a sample set of patient data, wherein: the machine learning model is trained using patient data for a plurality of patients, the sample set comprises a plurality of temporal windows, and for each respective temporal window of the plurality of temporal windows, the machine learning model is configured to determine a respective probability value in the set of sample probability values that indicates a probability that a cardiac arrhythmia occurred during the respective temporal window; generate graphical data based on the sample probability values; output a user interface for display on a display device, the user interface comprising the graphical data; receive, via the user interface, an indication of user input to select a probability threshold for a patient; receive patient data for the patient, wherein the patient data is collected by one or more medical devices; apply the machine learning model to the patient data to determine a current probability value that indicates a probability that the patient has experienced an occurrence of a cardiac arrhythmia; determine that the current probability value exceeds the probability threshold for the patient; and in response to determining that the current probability value is greater than or equal to the probability threshold for the patient, generate a notification indicating that the patient has likely experienced the occurrence of the cardiac arrhythmia.

In another aspect, this disclosure describes a computer-readable medium having instructions stored thereon that, when executed, cause one or more processing circuits of a computing system to generate a set of sample probability values by applying a machine learning model to a sample set of patient data, wherein: the machine learning model is trained using patient data for a plurality of patients, the sample set comprises a plurality of temporal windows, and for each respective temporal window of the plurality of temporal windows, the machine learning model is configured to determine a respective probability value in the set of sample probability values that indicates a probability that a cardiac arrhythmia occurred during the respective temporal window; generate graphical data based on the sample probability values; output a user interface for display on a display device, the user interface comprising the graphical data; receive, via the user interface, an indication of user input to select a probability threshold for a patient; receive patient data for the patient, wherein the patient data is collected by one or more medical devices; apply the machine learning model to the patient data to determine a current probability value that indicates a probability that the patient has experienced an occurrence of a cardiac arrhythmia; determine that the current probability value exceeds the probability threshold for the patient; and in response to determining that the current probability value is greater than or equal to the probability threshold for the patient, generate a notification indicating that the patient has likely experienced the occurrence of the cardiac arrhythmia.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
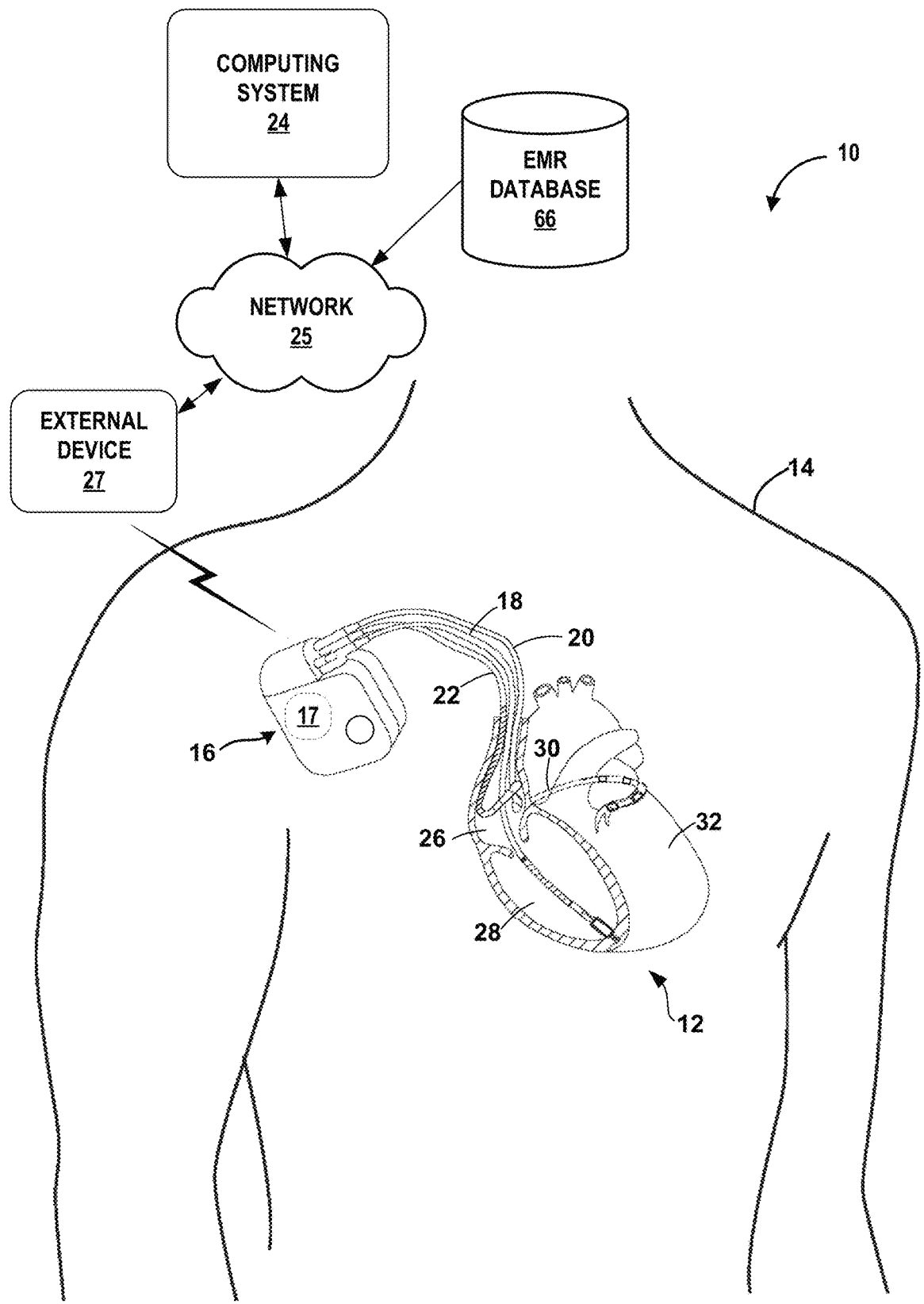
FIG. 1 is a block diagram illustrating a system for monitoring a patient for cardiac arrhythmias in accordance with the techniques of the disclosure.

FIG. 1 is a block diagram illustrating a system 10 for monitoring a patient for cardiac arrhythmias in accordance with the techniques of the disclosure. System 10 includes a medical device 16. One example of such a medical device is an implantable medical device (IMD), as shown in FIG. 1. As illustrated by example system 10 in FIG. 1, medical device 16 may, in some examples, be an implantable cardiac monitor, an implantable cardiac pacemaker, implantable cardioverter/defibrillator (ICD), or pacemaker/cardioverter/defibrillator, for example. In some examples, medical device 16 is a non-implantable medical device, such as a non-implantable cardiac monitor (e.g., a Holter monitor).

In the example of FIG. 1, medical device 16 is connected to leads 18, 20 and 22 and is communicatively coupled to external device 27, which in turn is communicatively coupled to computing system 24 over communication network 25. Medical device 16 senses electrical signals attendant to the depolarization and repolarization of heart 12, e.g., a cardiac electrogram (EGM), via electrodes on one or more leads 18, 20 and 22 or the housing of medical device 16. Medical device 16 may also deliver therapy in the form of electrical signals to heart 12 via electrodes located on one or more leads 18, 20 and 22 or a housing of medical device 16. The therapy may be pacing, cardioversion and/or defibrillation pulses. Medical device 16 may monitor EGM signals collected by electrodes on leads 18, 20 or 22, and based on the EGM signal, diagnose, and treat cardiac arrhythmias.

In some examples, medical device 16 includes communication circuitry 17 including any suitable circuitry, firmware, software, or any combination thereof for communicating with another device, such as external device 27 of FIG. 1. For example, communication circuitry 17 may include one or more processors, memory, wireless radios, antennae, transmitters, receivers, modulation and demodulation circuitry, filters, amplifiers, or the like for radio frequency communication with other devices, such as computing system 24. Medical device 16 may use communication circuitry 17 to receive downlinked data to control one or more operations of medical device 16 and/or send uplinked data to external device 27.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

While example system 10 of FIG. 1 depicts medical device 16, in other examples, the techniques of the disclosure may be applied to other types of medical devices that are not necessarily implantable. For example, a medical device in accordance with the techniques of the disclosure may include a wearable medical device or "smart" apparel worn by patient 14. For example, such a medical device may take the form of a wristwatch worn by patient 14 or circuitry that is adhesively affixed to patient 14, such as the Seeq™ Mobile Cardiac Telemetry System commercially available from Medtronic plc of Dublin, Ireland. In another example, a medical device as described herein may include an external medical device with implantable electrodes.

In some examples, external device 27 takes the form of an external programmer or mobile device, such as a mobile phone, a "smart" phone, a laptop, a tablet computer, a personal digital assistant (PDA), etc. In some examples, external device 27 is a CareLink™ monitor available from Medtronic, Inc. A user, such as a physician, technician, surgeon, electro-physiologist, or other clinician, may interact with external device 27 to retrieve physiological or diagnostic information from medical device 16. A user, such as patient 14 or a clinician as described above, may also interact with external device 27 to program medical device 16, e.g., select or adjust values for operational parameters of medical device 16. External device 27 may include processing circuitry, a memory, a user interface, and communication circuitry capable of transmitting and receiving information to and from each of medical device 16 and computing system 24.

In some examples, computing system 24 takes the form of a handheld computing device, computer workstation, server or other networked computing device, smartphone, tablet, or external programmer that includes a user interface for presenting information to and receiving input from a user. In some examples, computing system 24 may include one or more devices that implement a machine learning system, such as a neural network, a deep learning system, or another type of machine learning system. A user, such as a physician, technician, surgeon, electro-physiologist, or other clinician, may interact with computing system 24 to retrieve physiological or diagnostic information from medical device 16. A user may also interact with computing system 24 to program medical device 16, e.g., select values for operational parameters of the IMD. Computing system 24 may include a processor configured to evaluate EGM and/or other sensed signals transmitted from medical device 16 to computing system 24.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers and may thus form part of a large-scale public network infrastructure, e.g., the Internet. Network 25 may provide computing devices, such as computing system 24 and medical device 16, access to the Internet, and may provide a communication framework that allows the computing devices to communicate with one another. In some examples, network 25 may be a private network that provides a communication framework that allows computing system 24, medical device 16, and EMR database 66 to communicate with one another but isolates computing system 24, medical device 16, and EMR database 66 from external devices for security purposes. In some examples, the communications between computing system 24, medical device 16, and EMR database 66 are encrypted.

External device 27 and computing system 24 may communicate via wired and/or wireless communication over network 25 using any techniques known in the art. In some examples, computing system 24 is a remote device that communicates with external device 27 via an intermediary device located in network 25, such as a local access point, wireless router, or gateway. While in the example of FIG. 1, external device 27 and computing system 24 communicate over network 25, in some examples, external device 27 and computing system 24 communicate with one another directly. Examples of communication techniques may include, for example, communication according to the Bluetooth® or BLE protocols. Other communication techniques are also contemplated. Computing system 24 may also communicate with one or more other external devices using a number of known communication techniques, both wired and wireless. In some examples, computing system 24 and network 25 may implement and provide access to the Carelink™ system administered by Medtronic plc.

EMR database 66 stores EMR data for patient 14. EMR database 66 may include processing circuitry and one or more storage mediums (e.g., random access memory (RAM), read only memory (ROM), programmable read only memory (PROM), erasable programmable read only memory (EPROM), electronically erasable programmable read only memory (EEPROM), or flash memory. In some examples, EMR database 66 is a cloud computing system. In some examples, the functions of EMR database 66 are distributed across a number of computing systems.

In one example, computing system 24 receives patient data collected by medical device 16 of patient 14. In some examples, the patient data includes physiological data for patient 14, such as one or more of an activity level of patient 14, a heart rate of patient 14, a posture of patient 14, a cardiac electrogram of patient 14, a blood pressure of patient 14, a pulse transit time of patient 14, a respiration rate of patient 14, a hypopnea index or apnea of patient 14, accelerometer data for patient 14, features derived from accelerometer data of patient 14, such as activity counts, posture, statistical control process variables, etc., a raw electromyogram of patient 14, one or more features derived from a raw electromyogram of patient 14, such as heart rate variability, t-wave alternans, QRS morphology, etc., interval data and features derived from interval data, heart sounds, potassium levels, glycemic index, a temperature of patient 14, or any data derivable from the aforementioned parametric data, or any other types of patient parametric data. In some examples, medical device 16 and/or other devices may automatically generate the patient parametric data by processing information from one or more sensors. For example, sensors of medical device 16 and/or other devices may determine that patient 14 has fallen down, patient 14 is frail or suffers an illness, that patient 14 is suffering an instance of sleep apnea.

In some examples, the patient data includes environmental data such as, air quality measurements, ozone levels, particulate counts, or pollution levels proximate to patient 14, an ambient temperature, or daylight hours. In some examples, one of medical device or external device 27 may sense, via one or more sensors, the environmental data. In another example, the environmental data is received by external device 27 via an application, such as a weather application, executing on external device 27, and uploaded to computing system 24 over network 25. In another example, computing system 24 collects the environmental data directly from a cloud service that has location-based data for patient 14.

In some examples, the patient data includes patient symptom data that is uploaded by patient 14 via an external device, such as external device 27. For example, patient 14 may upload the patient symptom data via an application executing on a smart phone. In some examples, patient 14 may upload the upload the patient symptom data via a user interface (not depicted in FIG. 1), such as by touchscreen, keyboard, graphical user interface, voice commands, etc.

In some examples, the patient data includes device-related data, such as one or more of an impedance of one or more electrodes of the medical device, a selection of electrodes, a drug delivery schedule for the medical device, a history of electrical pacing therapy delivered to the patient, or diagnostic data for the medical device. In some examples, the medical device that collects the patient data is an IMD. In other examples, the medical device that collects the patient data is another type of patient device, such as a wearable medical device or a mobile device (e.g., a smartphone) of patient 14. In some examples, computing system 24 receives the patient data on a periodic, e.g., daily, basis.

In some examples, computing system 24 further receives EMR data for patient 14 from EMR database 66. The EMR data may be considered another form of patient data. In some examples, the EMR data stored by EMR database 66 may include many different types of historical medical information about patient 14. For example, EMR database 66 may store a medication history of the patient, a surgical procedure history of the patient, a hospitalization history of the patient, potassium levels of the patient over time, one or more lab test results for patient 14, a cardiovascular history of patient 14, or co-morbidities of patient 14 such as atrial fibrillation, heart failure, or diabetes, as examples.

Computing system 24 applies one or more machine learning models, trained using patient data for a plurality of patients, to the patient data for patient 14 to monitor patient 14 for occurrences of cardiac arrhythmias. For example, computing system 24 may receive patient data for patient 14. The patient data be collected by one or more medical devices, such as medical device 16. Furthermore, in this example, computing system 24 may apply a machine learning model to the patient data to determine a current probability value that indicates a probability that patient 14 has experienced an occurrence of a cardiac arrhythmia. In this example, computing system 24 may further determine whether the current probability value exceeds a probability threshold for patient 14. In response to determining that the current probability value is greater than or equal to the probability threshold for patient 14, computing system 24 may generate a notification indicating that patient 14 has likely experienced an occurrence of a cardiac arrhythmia. The probability value may be a value between 0 and 1; or a value in another range where the value is indicative of a probability or likelihood. Probability thresholds may be in such ranges as well.

How the probability threshold is set may determine a review burden and a diagnostic yield associated with notifications generated by computing system 24. A user who reviews the notifications generated by computing system 24 may experience a review burden associated with the notifications because the user may need to spend time reviewing the notifications and determining whether patient 14 actually experienced the cardiac arrhythmias indicated by the notifications. The diagnostic yield associated with the notifications may correspond to the percentage or other measures of how many of the notifications generated by computing system 24 actually yield valuable diagnostic information. Should the review burden be too great, it may be impractical for the user to use computing system 24 to monitor patient 14. Likewise, if the diagnostic yield is too low, the user may not find utility in using computing system 24 to monitor patient 14.

Hence, in accordance with techniques of this disclosure, computing system 24 may enable the user to adjust a probability threshold in a way that may change the review burden and diagnostic yield associated with notifications generated by computing system 24. Accordingly, in some examples of this disclosure, computing system 24 may generate a set of sample probability values by applying a machine learning model to a sample set of patient data. The machine learning model may be trained using patient data for a plurality of patients. Furthermore, the sample set may comprise a plurality of temporal windows. For each respective temporal window of the plurality of temporal windows, the machine learning model is configured to determine a respective probability value in the set of sample probability values that indicates a probability that a cardiac arrhythmia occurred during the respective temporal window. In some examples, each of the temporal windows of the sample set comprises a respective cardiac EGM strip.

Computing system 24 may generate graphical data based on the sample probability values and may output a user interface for display on a display device. The user interface may comprise the graphical data. As described in this disclosure, the graphical data may include one or more receiver-operator curves (ROCs), graphs, and/or other types of graphical data. Computing system 24 may receive, via the user interface, an indication of user input to select a probability threshold for patient 14. For instance, computing system 24 may receive indications of clicking, typing, tapping, sliding, dragging, pinching, or other types of user input directed to one or more features of the user interface. Computing system 24 may receive patient data for patient 14 and may apply the machine learning model to the patient data to determine a current probability value that indicates a probability that patient 14 has experienced an occurrence of a cardiac arrhythmia. Computing system 24 may then determine whether the current probability value exceeds the probability threshold set for patient 14.

In this example, in response to determining that the current probability value is greater than or equal to the probability threshold set for patient 14, computing system 24 may generate a notification indicating that patient 14 has likely experienced the occurrence of the cardiac arrhythmia. Computing system 24 may store copies of the generated notifications. By enabling the user to appropriately set the probability threshold, computing device 24 may not generate and store unneeded notifications. This may conserve storage space on computer-readable media of computing system 24. Furthermore, in some examples, computing system 24 may transmit the notifications to devices used by one or more users who are monitoring patient 14. By not generating and transmitting numbers of notifications inappropriate for the diagnostic purposes of the user, network bandwidth may be conserved and battery life of the receiving devices may be conserved.

Figure 2:
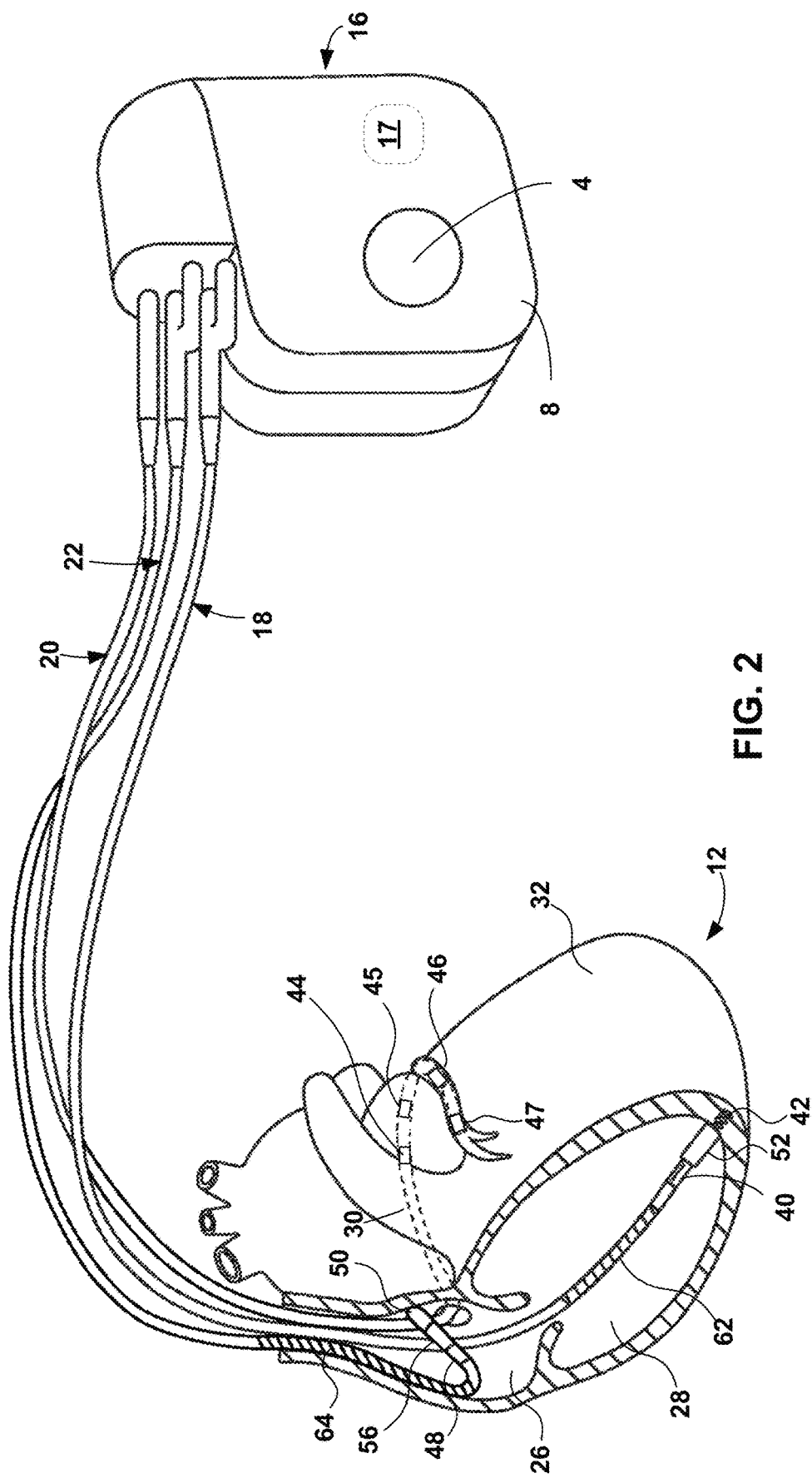
FIG. 2 is a conceptual diagram illustrating an implantable medical device (IMD) and leads of the system of FIG. 1 in greater detail.

FIG. 2 is a conceptual diagram illustrating medical device 16 and leads 18, 20, 22 of system 10 of FIG. 1 in greater detail. In the illustrated example, bipolar electrodes 40 and 42 are located adjacent to a distal end of lead 18, and bipolar electrodes 48 and 50 are located adjacent to a distal end of lead 22. In addition, four electrodes 44, 45, 46 and 47 are located adjacent to a distal end of lead 20. Lead 20 may be referred to as a quadrapolar LV lead. In other examples, lead 20 may include more or fewer electrodes. In some examples, LV lead 20 comprises segmented electrodes, e.g., in which each of a plurality of longitudinal electrode positions of the lead, such as the positions of electrodes 44, 45, 46 and 47, includes a plurality of discrete electrodes arranged at respective circumferential positions around the circumference of lead.

In the illustrated example, electrodes 40 and 44-48 take the form of ring electrodes, and electrodes 42 and 50 may take the form of extendable helix tip electrodes mounted retractably within insulative electrode heads 52 and 56, respectively. Leads 18 and 22 also include elongated electrodes 62 and 64, respectively, which may take the form of a coil. In some examples, each of electrodes 40, 42, 44-48, 50, 62, and 64 is electrically coupled to a respective conductor within the lead body of its associated lead 18, 20, 22 and thereby coupled to circuitry within medical device 16.

In some examples, medical device 16 includes one or more housing electrodes, such as housing electrode 4 illustrated in FIG. 2, which may be formed integrally with an outer surface of hermetically-sealed housing 8 of medical device 16 or otherwise coupled to housing 8. In some examples, housing electrode 4 is defined by an uninsulated portion of an outward facing portion of housing 8 of medical device 16. Other divisions between insulated and uninsulated portions of housing 8 may be employed to define two or more housing electrodes. In some examples, a housing electrode comprises substantially all of housing 8.

Housing 8 encloses signal generation circuitry that generates therapeutic stimulation, such as cardiac pacing, cardioversion, and defibrillation pulses, as well as sensing circuitry for sensing electrical signals attendant to the depolarization and repolarization of heart 12. Housing 8 may also enclose a memory for storing the sensed electrical signals. Housing 8 may also enclose communication circuitry 17 for communication between medical device 16 and computing system 24.

Medical device 16 senses electrical signals attendant to the depolarization and repolarization of heart 12 via electrodes 4, 40, 42, 44-48, 50, 62, and 64. Medical device 16 may sense such electrical signals via any bipolar combination of electrodes 40, 42, 44-48, 50, 62, and 64. Furthermore, any of the electrodes 40, 42, 44-48, 50, 62, and 64 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or extravascular (e.g., subcutaneous or substernal) leads not positioned within heart 12.

Medical device 16 send patient data to computing system 24 (e.g., by way of external device 27). The patient data may include data based on the electrical signals detected by electrodes 4, 40, 42, 44-48, 50, 62, and/or 64. For example, medical device 16 may gather and send cardiac EGM and other data to computing system 24. In accordance with the techniques of this disclosure, computing system 24 may use the patient data to determine probability values that indicate probabilities that patient 14 has experienced occurrences of one or more cardiac arrhythmias.

Although described herein in the context of an example medical device 16 that provides therapeutic electrical stimulation, the techniques for disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Figure 3:
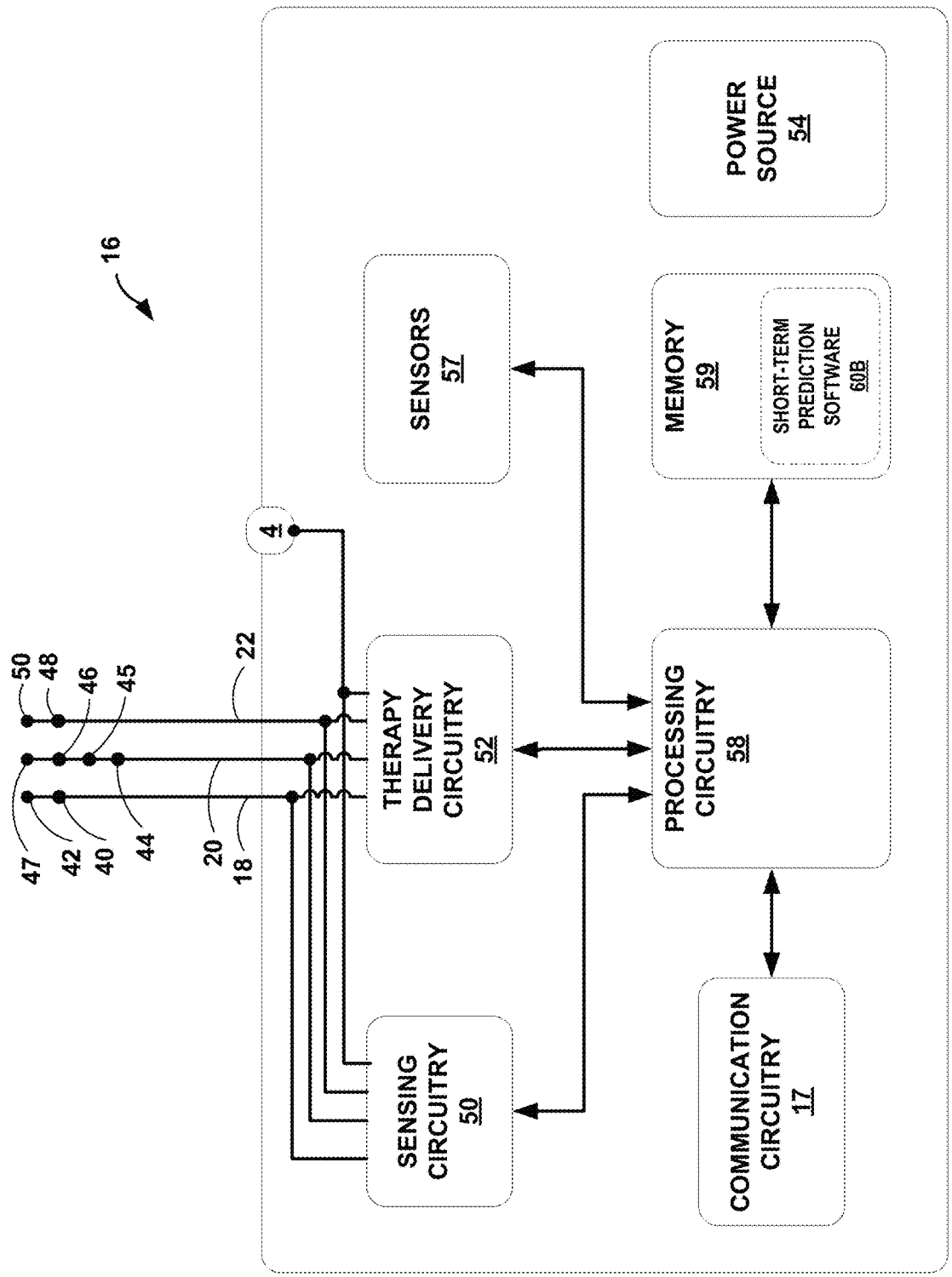
FIG. 3 is a block diagram of an example implantable medical device according to the techniques of the disclosure.

FIG. 3 is a block diagram of example medical device 16 according to the techniques of the disclosure. In the illustrated example, medical device 16 includes processing circuitry 58, memory 59, communication circuitry 17, sensing circuitry 50, therapy delivery circuitry 52, sensors 57, and power source 54. Memory 59 includes computer-readable instructions that, when executed by processing circuitry 58, cause medical device 16 and processing circuitry 58 to perform various functions attributed to medical device 16 and processing circuitry 58 herein (e.g., performing short-term prediction of cardiac arrhythmias, delivering therapy, such as anti-tachycardia pacing, bradycardia pacing, and post-shock pacing therapy, etc.). Memory 59 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 58 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 58 may include multiple components, such as any combination of one or more microprocessors, one or more controllers, one or more DSPs, one or more ASICs, or one or more FPGAs, as well as other discrete or integrated logic circuitry. The functions attributed to processing circuitry 58 herein may be embodied as software, firmware, hardware or any combination thereof.

Processing circuitry 58 controls therapy delivery circuitry 52 to deliver stimulation therapy to heart 5 according to therapy parameters, which may be stored in memory 59. For example, processing circuitry 58 may control therapy delivery circuitry 52 to deliver electrical pulses with the amplitudes, pulse widths, frequency, or electrode polarities specified by the therapy parameters. In this manner, therapy delivery circuitry 52 may deliver pacing pulses (e.g., ATP pulses, bradycardia pacing pulses, or post-shock pacing therapy) to heart 5 via electrodes 34 and 40. In some examples, therapy delivery circuitry 52 may deliver pacing stimulation, e.g., ATP therapy, bradycardia therapy, or post-shock pacing therapy, in the form of voltage or current electrical pulses. In other examples, therapy delivery circuitry 52 may deliver one or more of these types of stimulation in the form of other signals, such as sine waves, square waves, or other substantially continuous time signals.

Therapy delivery circuitry 52 is electrically coupled to electrodes 34 and 40 carried on the housing of medical device 16. Although medical device 16 may only include two electrodes, e.g., electrodes 34 and 40, in other examples, medical device 16 may utilize three or more electrodes. Medical device 16 may use any combination of electrodes to deliver therapy and/or detect electrical signals from patient 12. In some examples, therapy delivery circuitry 52 includes a charging circuit, one or more pulse generators, capacitors, transformers, switching modules, and/or other components capable of generating and/or storing energy to deliver as pacing therapy, cardiac resynchronization therapy, other therapy or a combination of therapies. In some examples, therapy delivery circuitry 52 delivers therapy as one or more electrical pulses according to one or more therapy parameter sets defining an amplitude, a frequency, a voltage or current of the therapy, or other parameters of the therapy.

Sensing circuitry 50 monitors signals from one or more combinations (also referred to as vectors) of two or more electrodes from among electrodes 4, 40, 42, 44-48, 50, 62 (FIG. 2), and 64 (FIG. 2) in order to monitor electrical activity of heart 12, impedance, or other electrical phenomenon. In some examples, sensing circuitry 50 includes one or more analog components, digital components or a combination thereof. In some examples, sensing circuitry 50 includes one or more sense amplifiers, comparators, filters, rectifiers, threshold detectors, analog-to-digital converters (ADCs) or the like. In some examples, sensing circuitry 50 converts sensed signals to digital form and provides the digital signals to processing circuitry 58 for processing or analysis. In one example, sensing circuitry 50 amplifies signals from electrodes 4, 40, 42, 44-48, 50, 62, and 64 and converts the amplified signals to multi-bit digital signals by an ADC.

In some examples, sensing circuitry 50 performs sensing of the cardiac electrogram to determine heart rates or heart rate variability, or to detect arrhythmias (e.g., tachyarrhythmias or bradycardia) or to sense other parameters or events from the cardiac electrogram. Sensing circuitry 50 may also include switching circuitry to select which of the available electrodes (and the electrode polarity) are used to sense the heart activity, depending upon which electrode combination, or electrode vector, is used in the current sensing configuration. Processing circuitry 58 may control the switching circuitry to select the electrodes that function as sense electrodes and their polarity. Sensing circuitry 50 may include one or more detection channels, each of which may be coupled to a selected electrode configuration for detection of cardiac signals via that electrode configuration. In some examples, sensing circuitry 50 compares processed signals to a threshold to detect the existence of atrial or ventricular depolarizations and indicate the existence of the atrial depolarization (e.g., P-waves) or ventricular depolarizations (e.g., R-waves) to processing circuitry 58. Sensing circuitry 50 may comprise one or more amplifiers or other circuitry for comparison of the cardiac electrogram amplitude to a threshold, which may be adjustable.

Processing circuitry 58 may include a timing and control module, which may be embodied as hardware, firmware, software, or any combination thereof. The timing and control module may comprise a dedicated hardware circuit, such as an ASIC, separate from other processing circuitry 58 components, such as a microprocessor, or a software module executed by a component of processing circuitry 58, which may be a microprocessor or ASIC. The timing and control module may implement programmable counters. If medical device 16 is configured to generate and deliver bradycardia pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Memory 59 may be configured to store a variety of operational parameters, therapy parameters, sensed and detected data, and any other information related to the therapy and treatment of patient 12. In the example of FIG. 3, memory 58 may store sensed cardiac EGMs, e.g., associated with detected or predicted arrhythmias, and therapy parameters that define the delivery of therapy provided by therapy delivery circuitry 52. In other examples, memory 58 may act as a temporary buffer for storing data until it can be uploaded to computing system 24.

Communication circuitry 17 includes any suitable circuitry, firmware, software, or any combination thereof for communicating with another device, such as computing system 24 via network 25 of FIG. 1. For example, communication circuitry 17 may include one or more antennae, modulation and demodulation circuitry, filters, amplifiers, or the like for radio frequency communication with other devices, such as computing system 24 via network 25. Under the control of processing circuitry 58, communication circuitry 17 may receive downlink telemetry from and send uplink telemetry to computing system 24 with the aid of an antenna, which may be internal and/or external. Processing circuitry 58 may provide the data to be uplinked to computing system 24 and the control signals for the telemetry circuit within communication circuitry 17, e.g., via an address/data bus. In some examples, communication circuitry 17 may provide received data to processing circuitry 58 via a multiplexer.

Power source 54 may be any type of device that is configured to hold a charge to operate the circuitry of medical device 16. Power source 54 may be provided as a rechargeable or non-rechargeable battery. In other example, power source 54 may incorporate an energy scavenging system that stores electrical energy from movement of medical device 16 within patient 12.

In accordance with the techniques of the disclosure, medical device 16 collects, via sensing circuitry 50 and/or sensors 57, patient data of patient 14. Sensors 57 may include one or more sensors, such as one or more accelerometers, pressure sensors, optical sensors for O2 saturation, etc. In some examples, the patient data includes one or more of an activity level of the patient, a heart rate of the patient, a posture of the patient, a cardiac electrogram of the patient, a blood pressure of the patient, accelerometer data for the patient, or other types of patient parametric data. Medical device 16 uploads, via communication circuitry 17, the patient parametric data to computing system 24 over network 25. In some examples, medical device 16 uploads the patient parametric data to computing system 24 on a daily basis. In some examples, the patient parametric data includes one or more values that represent average measurements of patient 14 over a long-term time period (e.g., about 24 hours to about 48 hours). For example, one or more other devices, such as a wearable medical device or a mobile device (e.g., a smartphone) of patient 14, may collect the patient parametric data and upload the patient parametric data to computing system 24.

Although described herein in the context of example medical device 16 that provides therapeutic electrical stimulation, the techniques for short-term prediction of cardiac arrhythmia disclosed herein may be used with other types of devices. For example, the techniques may be implemented with a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Figure 4:
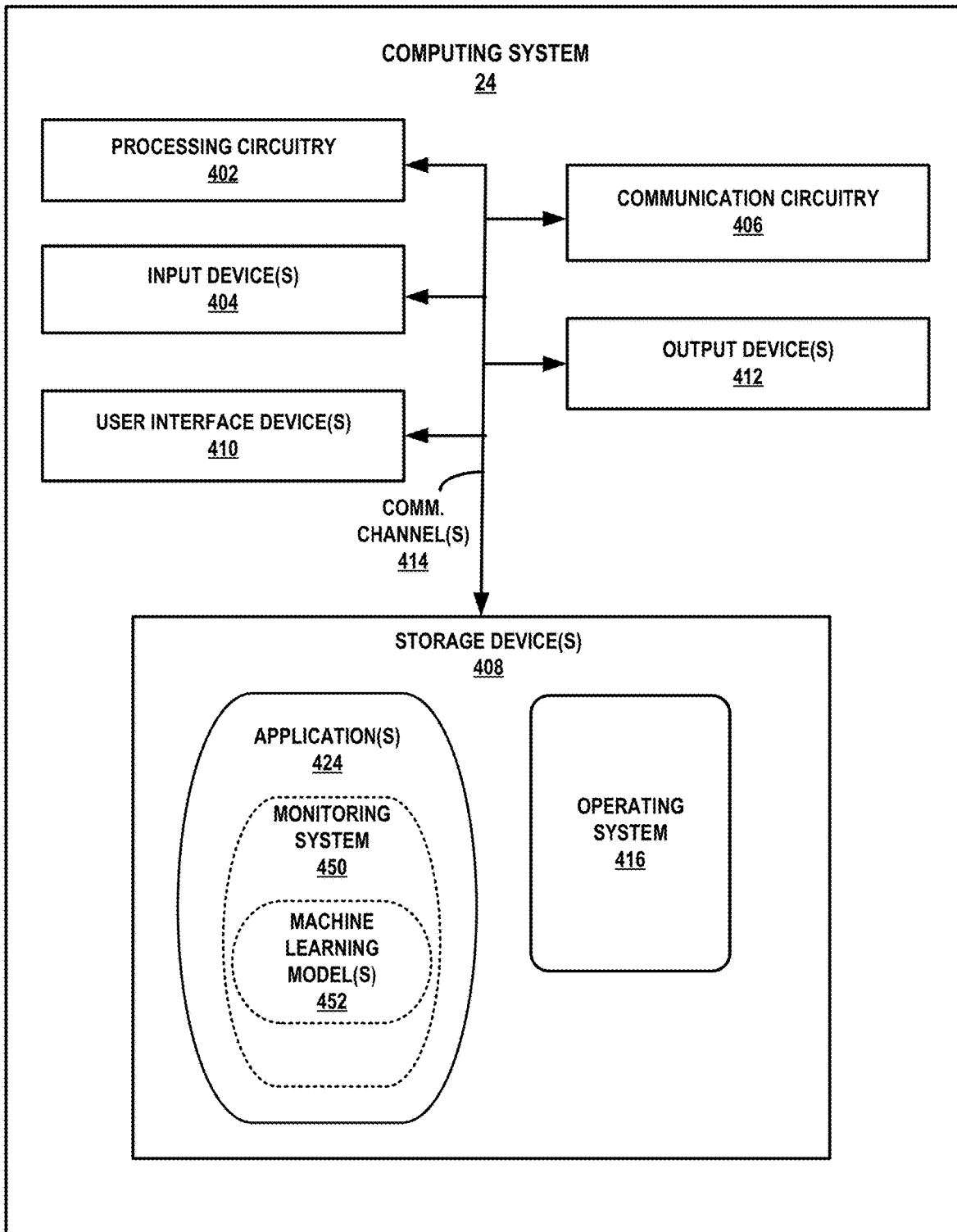
FIG. 4 is a block diagram illustrating an example computing device that operates in accordance with one or more techniques of the present disclosure.

FIG. 4 is a block diagram illustrating an example computing system 24 that operates in accordance with one or more techniques of the present disclosure. In one example, computing system 24 includes processing circuitry 402 for executing applications 424 that include monitoring system 450 or any other applications described herein. Although shown in FIG. 4 as a stand-alone computing system 24 for purposes of example, computing system 24 may be any component or system that includes processing circuitry or other suitable computing environment for executing software instructions and, for example, need not necessarily include one or more elements shown in FIG. 4 (e.g., communication circuitry 406; and in some examples components such as storage device(s) 408 may not be co-located or in the same chassis as other components). In some examples, computing system 24 may be a cloud computing system distributed across a plurality of devices.

As shown in the example of FIG. 4, computing system 24 includes processing circuitry 402, one or more input devices 404, communication circuitry 406, one or more output devices 412, one or more storage devices 408, and user interface (UI) device(s) 410. Computing system 24, in one example, further includes one or more application(s) 424 such as machine learning model(s) 450, and operating system 416 that are executable by computing system 24. Each of components 402, 404, 406, 408, 410, and 412 are coupled (physically, communicatively, and/or operatively) for inter-component communications. In some examples, communication channels 414 may include a system bus, a network connection, an inter-process communication data structure, or any other method for communicating data. As one example, components 402, 404, 406, 408, 410, and 412 may be coupled by one or more communication channels 414.

Processing circuitry 402, in one example, is configured to implement functionality and/or process instructions for execution within computing system 24. For example, processing circuitry 402 may be capable of processing instructions stored in storage device 408. Examples of processing circuitry 402 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 408 may be configured to store information within computing system 24 during operation. Storage device 408, in some examples, is described as a computer-readable storage medium. In some examples, storage device 408 is a temporary memory, meaning that a primary purpose of storage device 408 is not long-term storage. Storage device 408, in some examples, is described as a volatile memory, meaning that storage device 408 does not maintain stored contents when the computer is turned off. Examples of volatile memories include random access memories (RAM), dynamic random access memories (DRAM), static random access memories (SRAM), and other forms of volatile memories known in the art. In some examples, storage device 408 is used to store program instructions for execution by processing circuitry 402. Storage device 408, in one example, is used by software or applications 424 running on computing system 24 to temporarily store information during program execution.

Storage devices 408, in some examples, also include one or more computer-readable storage media. Storage devices 408 may be configured to store larger amounts of information than volatile memory. Storage devices 408 may further be configured for long-term storage of information. In some examples, storage devices 408 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing system 24, in some examples, also includes communication circuitry 406. Computing system 24, in one example, utilizes communication circuitry 406 to communicate with external devices, such as IMD 17 and EMR database 66 of FIG. 1. Communication circuitry 406 may include a network interface card, such as an Ethernet card, an optical transceiver, a radio frequency transceiver, or any other type of device that can send and receive information. Other examples of such network interfaces may include 3G, 4G, 5G, and WI-FI™ radios.

Computing system 24, in one example, also includes one or more user interface devices 410. User interface devices 410, in some examples, are configured to receive input from a user through tactile, audio, or video feedback. Examples of user interface devices(s) 410 include a presence-sensitive display, a mouse, a keyboard, a voice responsive system, video camera, microphone or any other type of device for detecting a command from a user. In some examples, a presence-sensitive display includes a touch-sensitive screen.

One or more output devices 412 may also be included in computing system 24. Output device 412, in some examples, is configured to provide output to a user using tactile, audio, or video stimuli. Output device 412, in one example, includes a presence-sensitive display, a sound card, a video graphics adapter card, or any other type of device for converting a signal into an appropriate form understandable to humans or machines. In some examples, output device(s) 412 include a display device. Additional examples of output device 412 include a speaker, a cathode ray tube (CRT) monitor, a liquid crystal display (LCD), or any other type of device that can generate intelligible output to a user.

Computing system 24 may include operating system 416. Operating system 416, in some examples, controls the operation of components of computing system 24. For example, operating system 416, in one example, facilitates the communication of one or more applications 424 and monitoring system 450 with processing circuitry 402, communication circuitry 406, storage device 408, input device 404, user interface devices 410, and output device 412.

Application 422 may also include program instructions and/or data that are executable by computing system 24. Example application(s) 422 executable by computing system 24 may include monitoring system 450. Other additional applications not shown may alternatively or additionally be included to provide other functionality described herein and are not depicted for the sake of simplicity.

In accordance with the techniques of the disclosure, applications 424 include a monitoring system 450. Monitoring system 450 is configured to receive patient data, evaluate the patient data, and generate notifications when monitoring system 450 determines that it is likely that patient 14 (FIG. 1) has experienced one or more occurrences of one or more cardiac arrhythmias.

As shown in the example of FIG. 4, monitoring system 450 may include a set of machine learning model(s) 452. Together, machine learning model(s) 452 may be referred to as a library of machine learning models or a suite of machine learning models. Each of machine learning model(s) 452 may be configured to generate, on the basis of patient data provided to the machine learning model, probability values that indicate probabilities of patient 14 having experienced occurrences of one or more cardiac arrhythmias. In some examples, each of machine learning model(s) 452 is implemented using one or more neural network systems, deep learning systems, or other type of supervised or unsupervised machine learning systems. For example, a machine learning model may be implemented by a feedforward neural network, such as a convolutional neural network, a radial basis function neural network, a recurrent neural network, a modular or associative neural network. In some examples, monitoring system 450 trains machine learning model(s) 452 with patient data for a plurality of patients to generate the probability values for cardiac arrhythmias. In some examples, after a machine learning model has been pre-trained with the patient data (and, in some examples, EMR data) for the plurality of patients, monitoring system 450 may further train the machine learning model with patient data specific to patient 14.

In some examples, monitoring system 450 trains one or more of machine learning model(s) 452 with the patient data for the plurality of patients, determines an error rate of the machine learning model, and then feeds the error rate back to the machine learning model so as to allow the machine learning model to update its predictions based on the error rate. Monitoring system 450 may use a backpropagation algorithm, such as a gradient descent algorithm, to feed to error rate back to the machine learning model. The error rate may correspond to differences between probability values determined by the machine learning model based on input data and prelabeled probability values for the same input data. In some examples, monitoring system 450 may use an error function to determine the error rate. The error function may be implemented using signal processing techniques and heuristics in the manner conventionally used to detect occurrences of cardiac arrhythmias. In some examples, the error function may return a vector of elements, each indicating whether the machine learning model correctly identified an occurrence of a respective cardiac arrhythmia.

In some examples, monitoring system 450 may receive, from patient 14 or a clinician, feedback indicating whether a predicted cardiac arrhythmia occurred in patient 14 within a particular time period. In some examples, monitoring system 450 may receive, from medical device 16, a message indicating that medical device 16 has detected (or has not detected) an occurrence of a cardiac arrhythmia in patient 14. In some examples, monitoring system 450 may obtain the feedback in other ways, such as by periodically checking the EMR data to determine if a cardiac arrhythmia occurred. Monitoring system 450 may update the machine learning model with the feedback. Thus, the training process may occur iteratively so as to incrementally improve the data generated by the machine learning model by "learning" from correct and incorrect data generated by the machine learning model in the past. Further, the training process may be used to further fine-tune a machine learning model that is trained using population-based data to provide more accurate predictions for a particular individual. In some examples, personnel of a monitoring service may provide the feedback.

In accordance with techniques of this disclosure, different ones of machine learning model(s) 452 may correspond to different monitoring reasons. In some examples, different ones of machine learning model(s) 452 correspond to different codes defined in the 10th revision of the International Statistical Classification of Diseases and Related Health Problems (ICD-10). Different ICD-10 codes may correspond to different reasons for prescribing medical device 16 to patient 14. For example, there may be different ICD-10 codes for atrial fibrillation (AF) management, stroke, syncope, and other medical conditions. In some examples, monitoring system 450 may train one or more of machine learning model(s) 452 using training data generated for different ICD-10 codes.

Monitoring system 450 may be used for different use-cases for which the same model might not provide optimal cardiac arrhythmia detection performance. Thus, a suite of machine learning models may be generated and applied to identify occurrences of cardiac arrhythmias of interest. For instance, in one example, machine learning model(s) 452 may include a machine learning model to detect any occurrences of AF or sinus bradycardia or asystole (e.g., pause) cardiac arrhythmias. In this example, the user may not be concerned about other cardiac arrhythmias (e.g., normal sinus rhythm (NSR), premature atrial contraction (PAC), premature ventricular contraction (PVC), sinus tachycardia) with respect to patient 14. In this example, this machine learning model may be used by a general practitioner to look for "important" arrhythmias. In another example, monitoring system 450 may use a machine learning model configured to determine probability values indicating probabilities that patient 14 has experienced any cardiac arrhythmias belonging to the sinus bradycardia or AV blocks types. In this example, the user may not be concerned above other arrhythmias with respect to patient 14. In this example, this machine learning model can be used for post transcatheter aortic valve replacement (TAVR) monitoring.

The input data used by machine learning model(s) 452 may include patient data. The patient data may include data representing one or more electrical signals, such as EGM signals. In some examples, the patient data may include data regarding the patient's physiological status (e.g., patient physiological statuses such as activity, posture, respiration, etc.), which may also be captured by medical device 16. Training data corresponding to different physiological conditions (e.g., rest, resting at night, resting at night with high posture angle, etc.) can be used as additional parameters for model training or input data for machine learning model(s) 452. Using such data may enable monitoring system 450 to detect cardiac arrhythmias during other disease conditions (e.g., a sensitive model for tachycardia during rest can be used to monitor heart failure (HF) patients; a model for bradycardia during activity can be used to monitor patients for chronotropic incompetence).

Once one or more of machine learning model(s) 452 have been trained, monitoring system 450 may use machine learning model(s) 452 to detect occurrences of cardiac arrhythmias experienced by patient 14. For example, monitoring system 450 (which may be executed by processing circuitry 402) may receive patient data via communication circuitry 406. The patient data may be collected in whole or part by medical device 16 of patient 14. In some examples, the patient data includes one or more of EGM data, an activity level of the patient, a heart rate of the patient, a posture of the patient, a cardiac electrogram of the patient, a blood pressure of the patient, accelerometer data for the patient, EMR data from EMR database 66, and/or other types of patient data. In some examples, medical device 16 is an IMD. In other examples, medical device that 16 is another type of patient device, such as a wearable medical device or a mobile device (e.g., a smartphone) of patient 14. In some examples, monitoring system 450 receives the patient data from medical device 16 on a daily basis.

In some examples, monitoring system 450 receives, via communication circuitry 406, EMR data for patient 14 from EMR database 66. In some examples, the EMR data stored by EMR database 66 may include many different types of historical medical information about patient 14. For example, EMR database 66 may store a medication history of the patient, a surgical procedure history of the patient, a hospitalization history of the patient, potassium levels of the patient over time, or one or more lab test results for the patient, etc. The EMR data may form part of the patient data used as input to one or more of machine learning model(s) 452.

In some examples, each of machine learning model(s) 452 converts the patient data into one or more vectors and tensors (e.g., multi-dimensional arrays) that represent the patient data. The machine learning model may apply mathematical operations to the one or more vectors and tensors to generate a mathematical representation of the patient data. The machine learning model may determine different weights that correspond to identified relationships between the patient data and the occurrence of cardiac arrhythmias. The machine learning model may apply the different weights to the patient data to generate the probability values.

Figure 5:
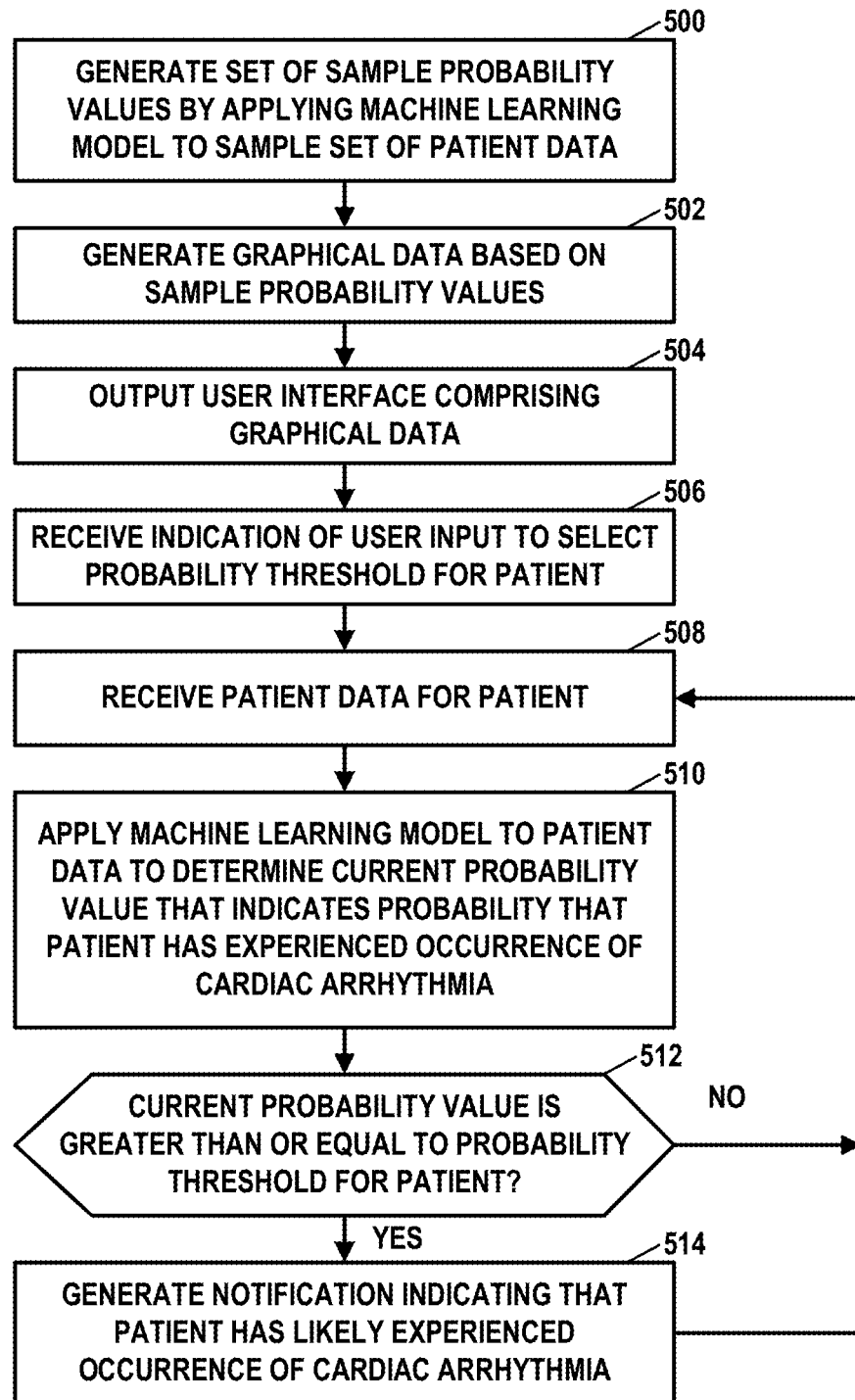
FIG. 5 is a flowchart illustrating an example operation in accordance with the techniques of the disclosure.

FIG. 5 is a flowchart illustrating an example operation in accordance with the techniques of the disclosure. For convenience, FIG. 5 is described with respect to FIG. 1. The flowcharts of this disclosure are presented as examples. Other examples in accordance with techniques of this disclosure may include more, fewer, or different actions, or actions may be performed in different orders or in parallel.

In the example of FIG. 5, computing system 24 may generate a set of sample probability values by applying a machine learning model to a sample set of patient data (500). The machine learning model may be one of machine learning models 452 (FIG. 4). As discussed above, the machine learning model may be trained using patient data for a set of sample patients. The set of sample patients may include a single sample patient or a plurality of sample patients. The set of sample patients may or may not include a current patient who is going to be monitored for one or more cardiac arrhythmias.

The sample set comprises a plurality of temporal windows. In some examples, the temporal windows overlap. In other examples, the temporal windows do not overlap. Each temporal window of the sample set may comprise one or more series of samples of at least one cardiac electrical waveform of a patient in the set of sample patients. In examples where the temporal windows overlap, the same sample may be in two or more temporal windows.

For each respective temporal window of the plurality of temporal windows, the machine learning model is configured to determine a respective probability value in the set of sample probability values that indicates a probability that a cardiac arrhythmia occurred during the respective temporal window. As discussed elsewhere in this disclosure, the machine learning model may comprise a neural network that has been trained to generate probability values indicating probabilities that a patient has experienced occurrences of one or more cardiac arrhythmias. Inputs to the neural network may include data corresponding to the respective temporal time window.

Figure 6:
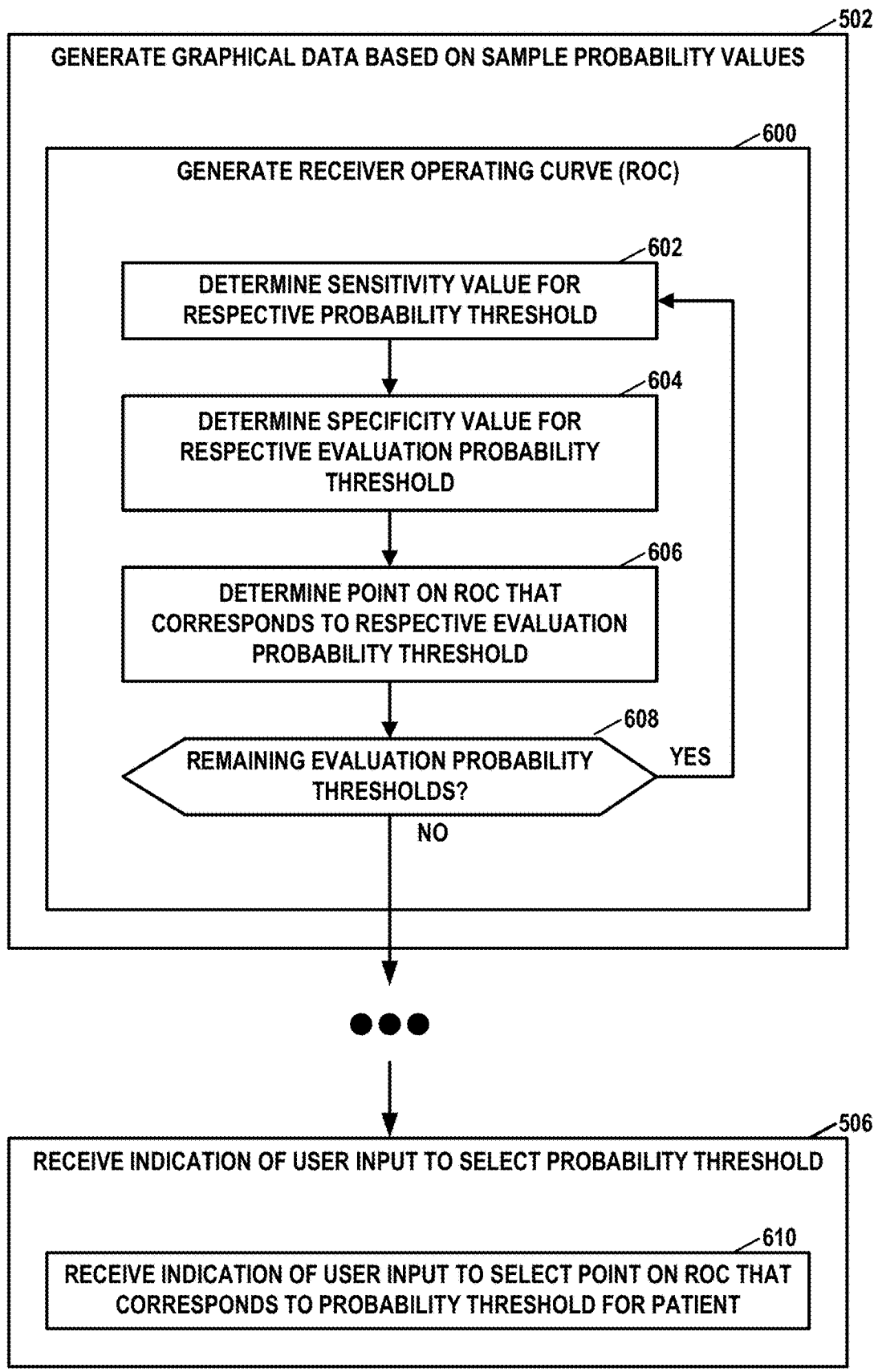
FIG. 6 is a flowchart illustrating a first example operation for generating graphical data and receiving an indication of user input to select a probability threshold, in accordance with techniques of this disclosure.
Figure 9:
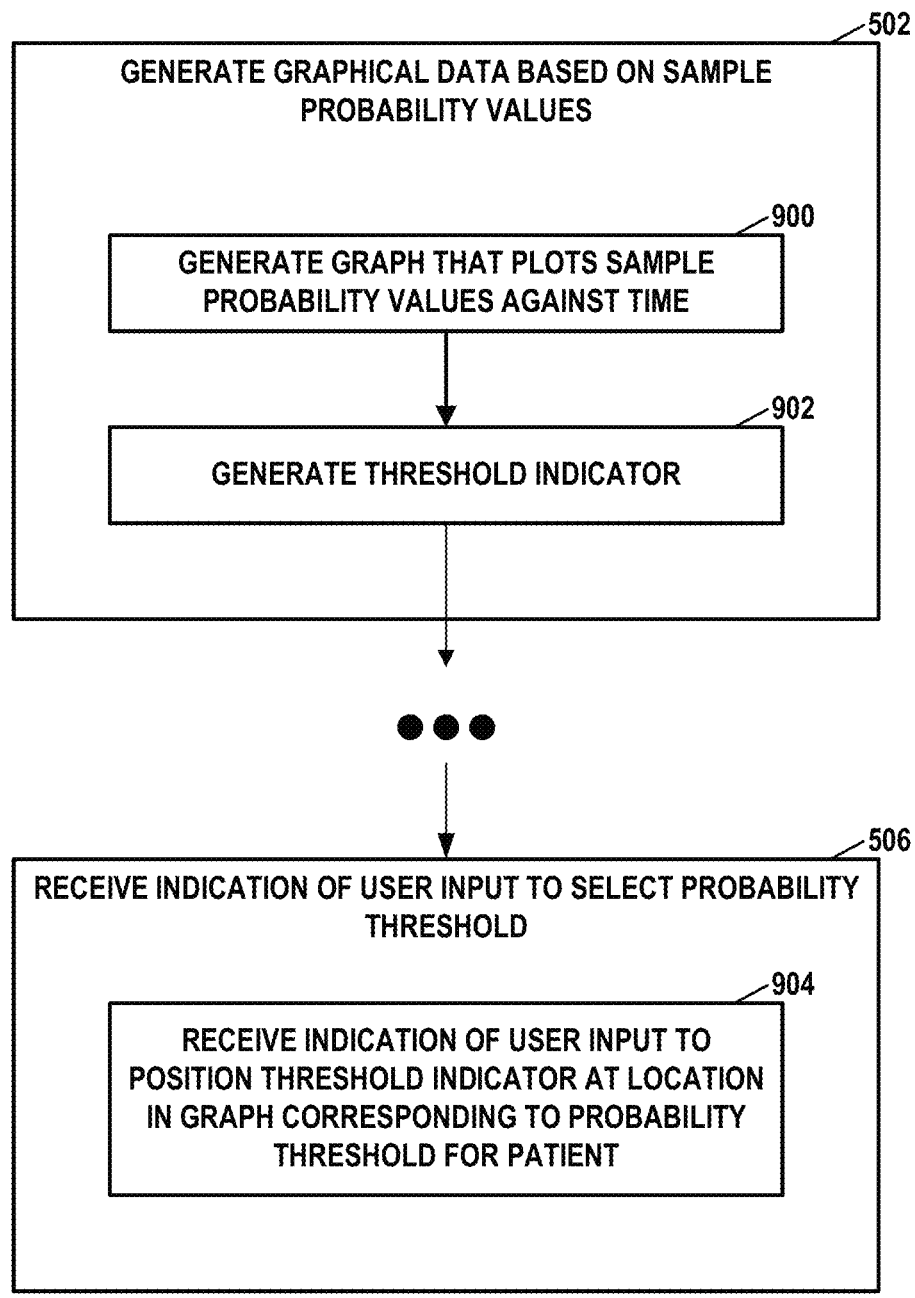
FIG. 9 is a flowchart illustrating a second example operation for generating graphical data and receiving an indication of user input to select a probability threshold, in accordance with techniques of this disclosure.

Furthermore, in the example of FIG. 5, computing system 24 may generate graphical data based on the sample probability values (502). As discussed elsewhere in this disclosure, computing system 24 may generate one or more of various types of graphical data based on the sample probability values. For instance, in some examples, computing system 24 generates a graphical representation of a ROC. FIG. 6, which is described in detail below, is an example flowchart that includes actions for generating a ROC. FIG. 9, which is also described in detail below, is an example flowchart that includes actions for generating a graph of probabilities of occurrences of cardiac arrhythmias plotted against time.

Computing system 24 may output a user interface for display on a display device (504). In the example of FIG. 5, the user interface comprises the graphical data. For instance, in an example where the graphical data comprises a ROC, the user interface may include a graph showing the ROC. In an example where the graphical data comprises a graph of probabilities of occurrences of cardiac arrhythmias plotted against time, the user interface may include the graph. The display device may be one of output device(s) 412, one of user interface device(s) 410, or another device for display data.

Computing system 24 may output the user interface in one or more of various forms. For example, computing system 24 may render and output a webpage that contains the graphical data. In another example, computing system 24 may output a graphical user interface for a local application.

Additionally, in the example of FIG. 5, computing system 24 may receive, via the user interface, an indication of user input to select a probability threshold for patient 14 (FIG. 1) (506). For instance, in an example where the user interface includes a graph showing the ROC, computer system 24 may receive an indication of user input to select a point on the ROC. In an example where the user interface includes a graph of probabilities of occurrences of cardiac arrhythmias plotted against time, the user interface may further include a threshold indicator and computing system 24 may receive an indication of user input to position the threshold indicator at a location in the graph corresponding to a probability threshold for patient 14. In some examples, computing system 24 does not require an indication of user input to select the probability threshold for patient 14. Rather, in the absence of an indication of user input to select the probability threshold for patient 14, computing system 24 may set the probability threshold to, or leave the probability threshold at, a default probability threshold. In some such examples, the default probability threshold may be a probability threshold that maximizes diagnostic yield irrespective of the anticipated review burden.

Computing system 24 may receive patient data for patient 14 (508). The patient data is collected by one or more medical devices, such as medical device 16 (FIG. 1), and/or other types of devices. As discussed elsewhere in this disclosure, the patient data may include one or more series of samples of at least one cardiac electrical waveform of patient 14.

Furthermore, in the example of FIG. 5, computing system 24 may apply the machine learning model to the patient data to determine a current probability value that indicates a probability that patient 14 has experienced an occurrence of a cardiac arrhythmia (510). For instance, in an example where the cardiac arrhythmia is atrial fibrillation, computing system 24 may apply the machine learning model to the patient data and determine that there is a 0.98 probability that patient 14 experienced an occurrence of atrial fibrillation.

Additionally, computing system 24 may determine whether the current probability value exceeds the probability threshold for patient 14 (512). In response to determining that the current probability value is greater than or equal to the probability threshold for patient 14 ("YES" branch of 512), computing system 24 may generate a notification indicating that the patient has likely experienced the occurrence of the cardiac arrhythmia (514). Computing system 24 may generate the notification in any of one or more ways. For instance, in one example, computing system 24 may send a message (e.g., a text message, SMS message, instant message, email message, in-app message, voice message, video message, etc.) to a monitoring user. In this example, the message notifies the monitoring user that patient 14 likely experienced an occurrence of the cardiac arrhythmia. In some examples, computing system 24 does not generate a notification for each occurrence of a cardiac arrhythmia but may instead generate notifications for groups of occurrences of cardiac arrhythmias. In some examples, a user interface may present a list of the generated notifications.

Otherwise, in the example of FIG. 5, in response to determining that the current probability value is not greater than or equal to the probability threshold for patient 14 ("NO" branch of 512), computing system 24 does not generate the notification and may continue to receive patient data for the patient (508). In other examples, computing system 24 may perform other actions in response to determining that the current probability value is not greater than or equal to the probability threshold for patient 14. In some examples, computing system 24 may perform the operation of FIG. 5 for each respective cardiac arrhythmia in a plurality of cardiac arrhythmias.

As noted above, in some examples, computing system 24 does not receive an indication of user input to select the probability threshold for a patient, such as patient 14. Thus, in such examples, computing system 24 may receive patient data for a patient, wherein the patient data is collected by one or more medical devices. In this example, computing system 24 may apply the machine learning model to the patient data to determine a current probability value that indicates a probability that the patient has experienced an occurrence of the cardiac arrhythmia. Furthermore, in this example, computing system 24 may determine that the current probability value exceeds a default probability threshold, wherein the default probability threshold is set to maximize diagnostic yield. In response to determining that the current probability value is greater than or equal to the default probability threshold, computing system 24 may generate a notification indicating that the patient has likely experienced the occurrence of the cardiac arrhythmia.

FIG. 6 is a flowchart illustrating a first example operation for generating graphical data and receiving an indication of user input to select a probability threshold, in accordance with techniques of this disclosure. The example of FIG. 6 provides example details regarding how computing system 24 may generate graphical data in action (502) of FIG. 5 and how computing system 24 may receive an indication of user input to select a probability threshold for patient 14 in action (506) of FIG. 5.

In the example of FIG. 6, as part of generating graphical data based on the sample probability values, computing system 24 may generate a ROC (600). The ROC is a curve that plots sensitivity values against specificity values. In general, when sensitivity values are high, the probability of computing system 24 not generating a notification indicating that patient 14 experienced an occurrence of the cardiac arrhythmia when patient 14 actually experienced an occurrence of the cardiac arrhythmia is low. Thus, when sensitivity values are high, there may be more false positives, but computing system 24 is unlikely to miss occurrences of the cardiac arrhythmia. When specificity values are high, the probability of computing system 24 generating a notification indicating that patient 14 experienced an occurrence of the cardiac arrhythmia when patient 14 did not actually experience an occurrence of the cardiac arrhythmia is low. Thus, when specificity values are high, there are likely to be few false positives, but computing system 24 is likely to miss more occurrences of the cardiac arrhythmia. Accordingly, the sensitivity values decrease as specificity values increase, and vice versa.

As part of generating the ROC, computing system 24 may perform actions (602) through (608) for each respective probability threshold in a set of evaluation probability thresholds. The set of evaluation probability thresholds may include two or more evaluation probability thresholds. In general, the greater number of evaluation probability thresholds used, the more data is available to computing system 24 to generate the ROC.

In the example of FIG. 6, computing system 24 may determine a sensitivity value for a respective evaluation probability threshold (602). As discussed above with respect to FIG. 5, computing system 24 may generate a set of sample probability values by applying a machine learning mode to a sample set of patient data. Each of the sample probability values indicates a probability that an occurrence of the cardiac arrhythmia happened during the respective temporal window. Computing system 24 may determine the sensitivity value for the respective evaluation probability threshold as a ratio of: (i) a total number of sample probability values in the set of sample probability values that are greater than or equal to the respective evaluation probability threshold to (ii) a total number of temporal windows in the sample set that actually contain occurrences of the cardiac arrhythmia.

Furthermore, in the example of FIG. 6, computing system 24 may determine a specificity value for the respective evaluation probability threshold (604). Computing system 24 may determine the specificity value for the respective evaluation probability threshold as a ratio of: (i) the total number of the sample probability values that are not greater than or equal to the respective evaluation probability threshold to (ii) the total number of the temporal windows in the sample set that do not actually contain occurrences of the cardiac arrhythmia.

Computing system 24 may then determine a point on the ROC that corresponds to the respective probability value (606). The point on the ROC that corresponds to the respective probability value is based on the sensitivity value for the respective probability threshold and the specificity value for the respective probability threshold. For instance, the point may be defined by a pair of coordinates, one of which is the sensitivity value for the respective probability threshold and one of which is the specificity value for the respective evaluation probability threshold. In some examples, computing system 24 may apply one or more functions to transform the sensitivity value and specificity value for the respective evaluation probability threshold to determine the coordinates of the point.

Computing system 24 may determine whether there are any remaining evaluation probability thresholds to evaluate (608). If there are any remaining evaluation probability thresholds to evaluate ("YES" branch of 608), computing system 24 may repeat actions (602) through (606) with respect to another one of the evaluation probability thresholds. Otherwise ("NO" branch of 608), computing system 24 may continue the operation of FIG. 5. In some examples, after determining that there are no remaining evaluation probability thresholds to evaluate, computing system 24 may generate (e.g., using interpolation, extrapolation, and/or regression) a smooth or discrete-valued curve based on the determined points.

Subsequently, computing system 24 may receive an indication of user input to select a probability threshold for patient 14 (506). In the example of FIG. 6, as part of receiving the indication of user input to select the probability threshold for patient 14, computing system 24 may receive an indication of user input to select a point on the ROC that corresponds to the probability threshold for patient 14 (610). Computing system 24 may receive the indication of user input to select the point on the ROC in one of various ways. For instance, in one example, the user interface may include an indicator element that is slidable along the ROC. In this example, computing system 24 may receive tapping, sliding, or dragging input to reposition the indicator element to a position along the ROC. In some examples, computing system 24 may receive an indication of user input specifying the probability threshold for patient 14, in which case, computing system 24 may update the position of the indicator element such that the indicator element is located at a position on the ROC corresponding to the specified probability threshold for patient 14. In some examples, computing system 24 may receive an indication of user input specifying a sensitivity value or a specificity value, in which case, computing system 24 may update the position of the indicator element such that the indicator element is located at a position on the ROC corresponding to the specified sensitivity value or the specified specificity value.

Figure 7:
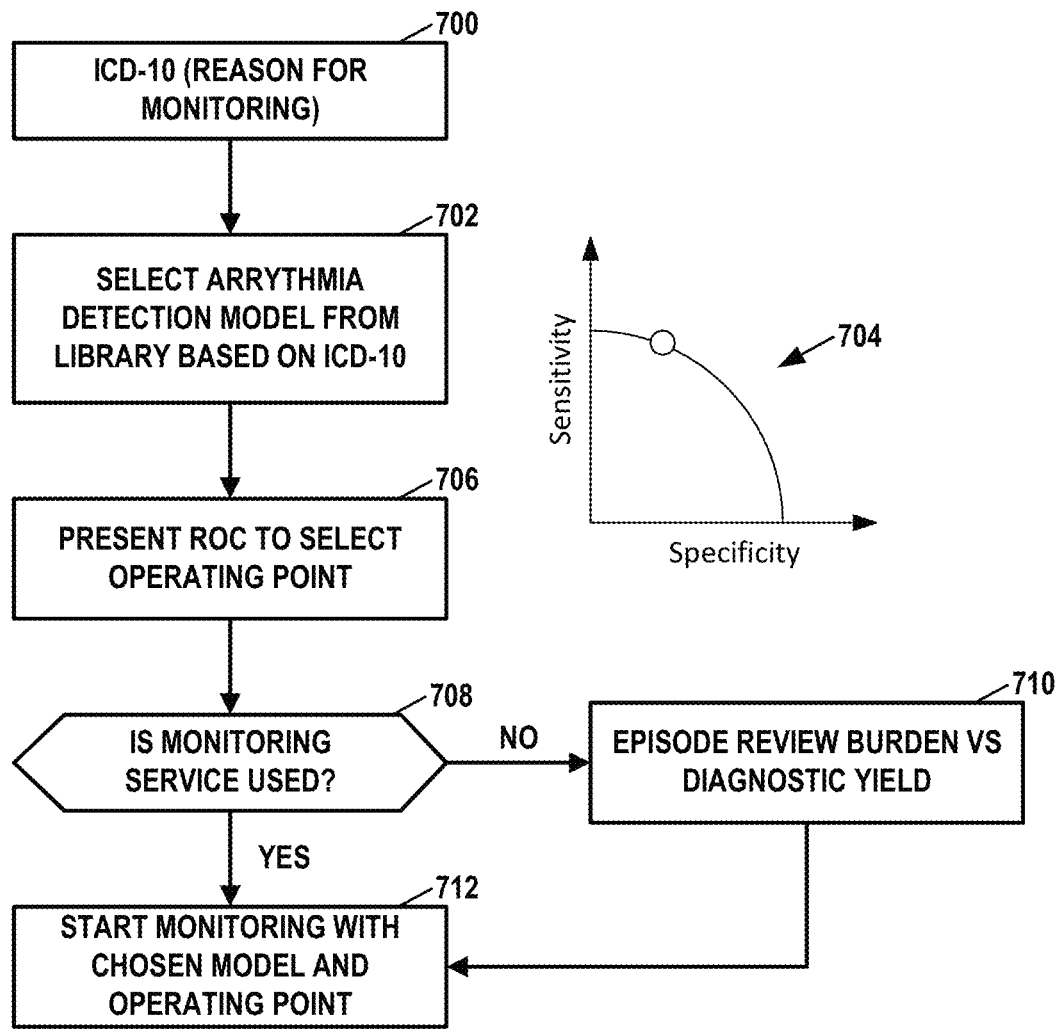
FIG. 7 is a flowchart illustrating an example process for model and operating point selection based on a reason for monitoring, in accordance with techniques of this disclosure.

FIG. 7 is a flowchart illustrating an example process for model and operating point selection based on a reason for monitoring, in accordance with techniques of this disclosure. A user may determine an ICD-10 code corresponding to a reason for monitoring patient 14 (700). Furthermore, computing system 24 may be configured to use a set of machine learning models. The set of machine learning models may be referred to as a library of machine learning models. Each machine learning model may include one or more neural networks configured to determine probability values for one or more cardiac arrhythmias. Each of the machine learning models may be associated with a different ICD-10 code, or otherwise associated with a different reason for monitoring the patient. Computing system 24 and/or the user may select a machine learning model in the library based on the ICD-10 code associated with the machine learning model (702).

Furthermore, in the example of FIG. 7, computing system 24 may present a ROC 704 to the user to enable the user to select one or more operating points (706). An operating point may correspond to a probability threshold for patient 14. Computing system 24 may generate the ROC based on thresholding the arrhythmia likelihood (e.g., as described in the example of FIG. 6). For example, if the reason for monitoring is to detect atrial fibrillation (AF) in stroke patients, computing system 24 may present a ROC for AF detection from which the user (e.g., a prescribing physician) can choose a threshold that corresponds to a very high sensitivity and low-specificity for AF detection. In another example, if the reason for monitoring is AF management, the user (e.g., a prescribing physician) can choose, from the ROC, an operating point that has a high specificity and low sensitivity for AF. In another example, if the reason for monitoring is syncope, the physician can choose a high sensitivity for asystole and sinus brady and a balanced sensitivity and specificity for AF and other arrhythmias from the ROC.

In the example of FIG. 7, the user (e.g., the prescribing physician) may iterate on a review burden versus diagnostic yield for the chosen machine learning models and operating points. As discussed elsewhere in this disclosure, review burden may refer to the burden of reviewing notifications and diagnostic yield may refer to the amount of diagnostically valuable information derived from such notifications. For instance, if the user is not using a monitoring service ("NO" branch of 708), the user may evaluate the review burden versus the diagnostic yield one or more times before settling on an acceptable balance between review burden and diagnostic yield.

In some examples, computing system 24 may present (e.g., output for display on a display device) data indicating the anticipated review burden versus the anticipated diagnostic yield for one or more operating points. An operating point for a cardiac arrhythmia may correspond to a probability threshold. In some examples, computing system 24 may store historical data (e.g., from a monitoring center or database) for a patient population. For each patient in the patient population, the historical data may indicate an operating point for the patient, a review burden for the patient, and a diagnostic yield for the patient. In this example, when an operating point is being set for a particular patient, computing system 24 may identify similar patients in the patient population with whom the operating point was used and determine the anticipated review burden and anticipated diagnostic yield for the particular patient based on review burdens and diagnostic yields of the identified patients. For instance, computing system 24 may calculate averages of the review burdens and diagnostic yields of the identified patients.

In some examples, computing system 24 may estimate the anticipated review burden and anticipated diagnostic yield for an operating point from prevalence and algorithm performance numbers. For instance, in one example, suppose the patient population being monitored has an AF prevalence of 20% (i.e., 20% of AF-triggered ECGs from patients in this population actually have AF). This prevalence can be obtained either from the literature or from historical values at the monitoring center. Furthermore, in this example, suppose that a user would like to get a diagnostic yield and review burden for 2 AF detection operating points (i) 95% sensitivity and 70% specificity and (ii) 70% sensitivity and 95% specificity, and the corresponding algorithm-detected AF episodes are reported. An AF episode may correspond to a temporal window in which a device (e.g., medical device 16) reported that an AF might be present. In this example, the "baseline" review burden is where all episodes are reviewed. In this example, with the first operating point, the review burden is 43% of the baseline. That is, assume 1000 episodes are presented to the algorithm. Accordingly, the number of true positives (TP) among the 1000 episodes is expected to be TP=0.95*200=190; the number of false positives (FP) among the 1000 episodes is expected to be FP=(1−0.7)*800=240; the total number of detections=190+240=430; hence 430/1000=43%. 95% (190 out of 200) of the actual episodes are captured and about 44% (190 out of 430) of the reviewed episodes are true AF. With the second operating point, the review burden is 18% of the baseline. That is, assume 1000 episodes being presented to the algorithm; TP=0.7*200=140; FP=(1−0.95)*800=40; total detections=140+40=180; hence, 180/1000=18%. Here, only 70% (140 out of 200) of the actual episodes are captured and about 78% (140 out of 180) of the reviewed episodes are true AF. Thus, in this example, the review burden and diagnostic yield for the first operating point is higher than that of the second one.

In some examples, the user may adjust the review burden versus the diagnostic yield of the chosen cardiac arrhythmias by changing the probability thresholds for one or more of the chosen cardiac arrhythmias (e.g., in the manner described elsewhere in this disclosure). This step can help users (e.g., physicians) tune their operating models to best choose one that provides optimal balance between review burden and diagnostic yield (e.g., the review burden might be exceedingly high if the sensitivity (e.g., probability threshold) is set at 99% but might be manageable if the sensitivity is set at 98%). Computing system 24 may then use the chosen model and operating points are used for arrhythmia detection and notification.

If the user is using a monitoring service ("YES" branch of 708) or after evaluating the reviewing burden versus diagnostic yield, computing system 24 may start a monitoring process with the chosen machine learning model(s) and operating point. The monitoring process may receive patient information, apply the selected machine learning model, and generate notifications (e.g., as described with respect to actions (508) through (514) of FIG. 5. The monitoring service may be a service that reviews notifications on behalf of the user (e.g., physician).

Figure 8:
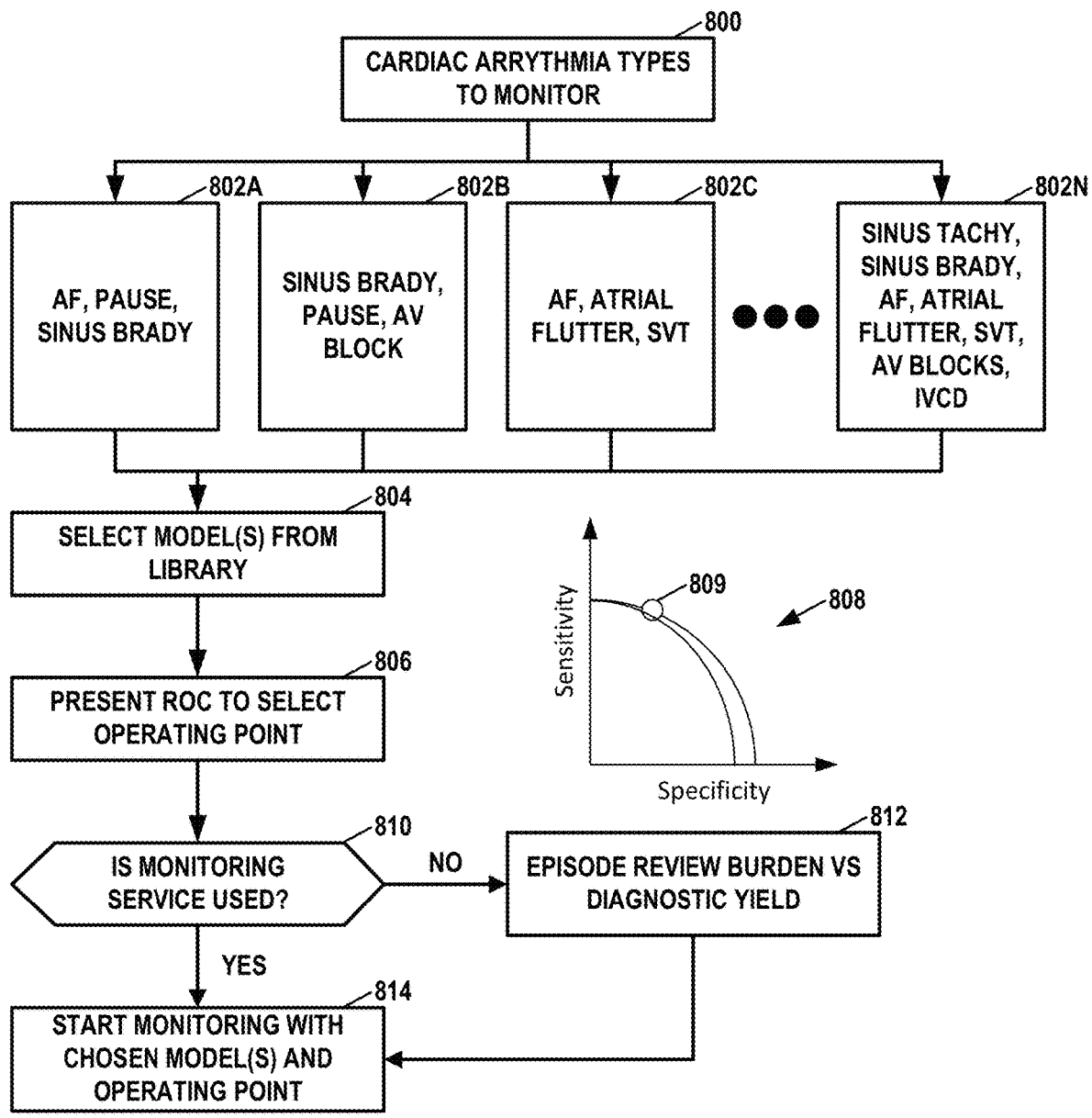
FIG. 8 is a flowchart illustrating an example process for model and operating point selection based on cardiac arrhythmias for monitoring, in accordance with techniques of this disclosure.

FIG. 8 is a flowchart illustrating an example process for model and operating point selection based on cardiac arrhythmias for monitoring, in accordance with techniques of this disclosure. In the example of FIG. 8, a user (e.g., a prescribing physician) may determine a set of cardiac arrhythmias to monitor (800). The set of cardiac arrhythmias to monitor may be those cardiac arrhythmias for which the user wants to receive notifications. In this way, the user may choose one or more cardiac arrhythmias from a set of cardiac arrhythmias. The chosen cardiac arrhythmias may be cardiac arrhythmias that the user is interested in monitoring.

Furthermore, as shown in the example of FIG. 8, machine learning models 802A-802N (collectively, "machine learning models 802") may be developed for different groups of cardiac arrhythmias. For instance, machine learning model 802A may generate probability values indicating probabilities that patient 14 has experienced occurrences of atrial fibrillation (AF), pause, and sinus bradycardia (sinus brady); machine learning model 802B may generate probability values indicating probabilities that patient 14 has experienced occurrences of sinus bradycardia, pause, and atrioventricular (AV) block; machine learning model 802C may generate probability values indicating probabilities that patient 14 has experienced occurrences of atrial fibrillation, atrial flutter, and supraventricular tachycardia (SVT); machine learning model 802N may generate probability values indicating probabilities that patient 14 has experienced occurrences of sinus tachycardia (sinus tachy), sinus bradycardia (sinus brady), atrial fibrillation (AF), atrial flutter, supraventricular tachycardia (SVT), atrioventricular (AV) blocks, and intraventricular conduction delay (IVCD). In the example of FIG. 8, each of machine learning models 802 corresponds to a different class of cardiac arrhythmias. In other examples, there may be different machine learning models for different cardiac arrhythmias instead of different classes of cardiac arrhythmias. In some examples, each of machine learning models 802 may be a different one of machine learning models 452 (FIG. 4). Each of machine learning models 802 may be implemented using one or more neural networks. The developed machine learning models 802 may together form a "library" of machine learning models.

The user may select one or more of machine learning models from the library of machine learning models 802 (804). For instance, if the user chooses to monitor sinus bradycardia, AV block, and atrial flutter, the user may choose machine learning models 802B and 802C. Note that in some instances, the selected machine learning models may be configured to generate probability value for one or more cardiac arrhythmias that the user does not necessarily want to monitor. In some examples, computing system 24 may receive an indication of user input to select one or more of machine learning models 802 from the library of machine learning models 802.

Furthermore, in the example of FIG. 8, computing system 24 may present one or more ROCs 808 to the user to enable the user to select one or more operating points for patient 14 (806). Each of the operating points for patient 14 may correspond to the probability threshold for use in identifying occurrences of different cardiac arrhythmias. Thus, based on the chosen cardiac arrhythmias for monitoring, the corresponding machine learning models may be chosen and the corresponding ROCs may be presented to enable the user to select an operating point. The user may select a different operating point on each of the ROCs. In the example of FIG. 8, the user may select an operating point on a ROC by providing user input to move an indicator element 809 on the ROC, thereby providing computing system 24 with an indication of user input to select a point on the ROC that corresponds to the probability threshold of patient 14 for the cardiac arrhythmia.

In the example of FIG. 8, the user (e.g., the prescribing physician) may iterate on a review burden versus diagnostic yield for the chosen machine learning models and operating point. As discussed elsewhere in this disclosure, review burden may refer to the burden of reviewing notifications and diagnostic yield may refer to the amount of diagnostically valuable information derived from such notifications. For instance, if the user is not using a monitoring service ("NO" branch of 810), the user may evaluate the review burden versus the diagnostic yield one or more times before settling on an acceptable balance between review burden and diagnostic yield. In some examples, the user may adjust the review burden versus the diagnostic yield by changing the probability thresholds for one or more of the chosen cardiac arrhythmias (e.g., in the manner described elsewhere in this disclosure). If the user is using a monitoring service ("YES" branch of 810) or after evaluating the reviewing burden versus diagnostic yield, computing system 24 may start a monitoring process with the chosen machine learning model(s) and operating point. The monitoring process may receive patient information, apply the selected machine learning model, and generate notifications (e.g., as described with respect to actions (508) through (514) of FIG. 5. In some examples, computing system 24 may receive subsequent indications of user input to update the probability threshold for patient 14.

FIG. 9 is a flowchart illustrating a second example operation for generating graphical data and receiving an indication of user input to select a probability threshold, in accordance with techniques of this disclosure. The example of FIG. 9 provides example details regarding how computing system 24 may generate graphical data in action (502) of FIG. 5 and how computing system 24 may receive an indication of user input to select a probability threshold for patient 14 in action (506) of FIG. 5.

As shown in the example of FIG. 9, as part of generating graphical data based on the sample probability values, computing system 24 may generate a graph that plots sample probability values against time (908). As discussed above with respect to FIG. 5, computing system 24 may generate a set of sample probability values by applying a machine learning model to a sample set of patient data. Each of the sample probability values indicates a probability that a cardiac arrhythmia belonging to a cardiac arrhythmia occurred during the respective temporal window. In some examples, computing system 24 may generate a smooth or discrete curve based on the sample probability values.

Furthermore, in the example of FIG. 9, computing system 24 may generate a threshold indicator (902). Additionally, in the example of FIG. 9, as part of receiving an indicator of user input to select the probability threshold for patient 14 (506), computing system 24 may receive an indication of user input to position the threshold indicator at a location in the graph corresponding to the probability threshold for patient 14 (904).

Computing system 24 may generate the threshold indicator in any of one or more ways. For instance, in one example, the threshold indicator comprises a threshold bar superimposed on the graph and oriented parallel to a time axis of the graph. In this example, the threshold bar may be superimposed on the graph such that the threshold bar appears over or underneath a curve or data points based on the set of sample probability values. Furthermore, in some examples where the threshold indicator comprises a threshold bar, computing system 24 may receive indications of user input to slide the threshold bar in a direction perpendicular to the time axis in order to position the threshold indicator at a location in the graph corresponding to the desired probability threshold for patient 14. In some examples, computing system 24 may receive an indication of user input to specify the desired probability threshold for patient 14 (e.g., in the form of text) and computing system 24 may update the location of the threshold indicator to a location in the graph corresponding to the desired probability threshold for patient 14. In some examples, the threshold indicator may comprise an arrow, pointer, or other type of graphical element in or adjacent to the graph.

Figure 10:
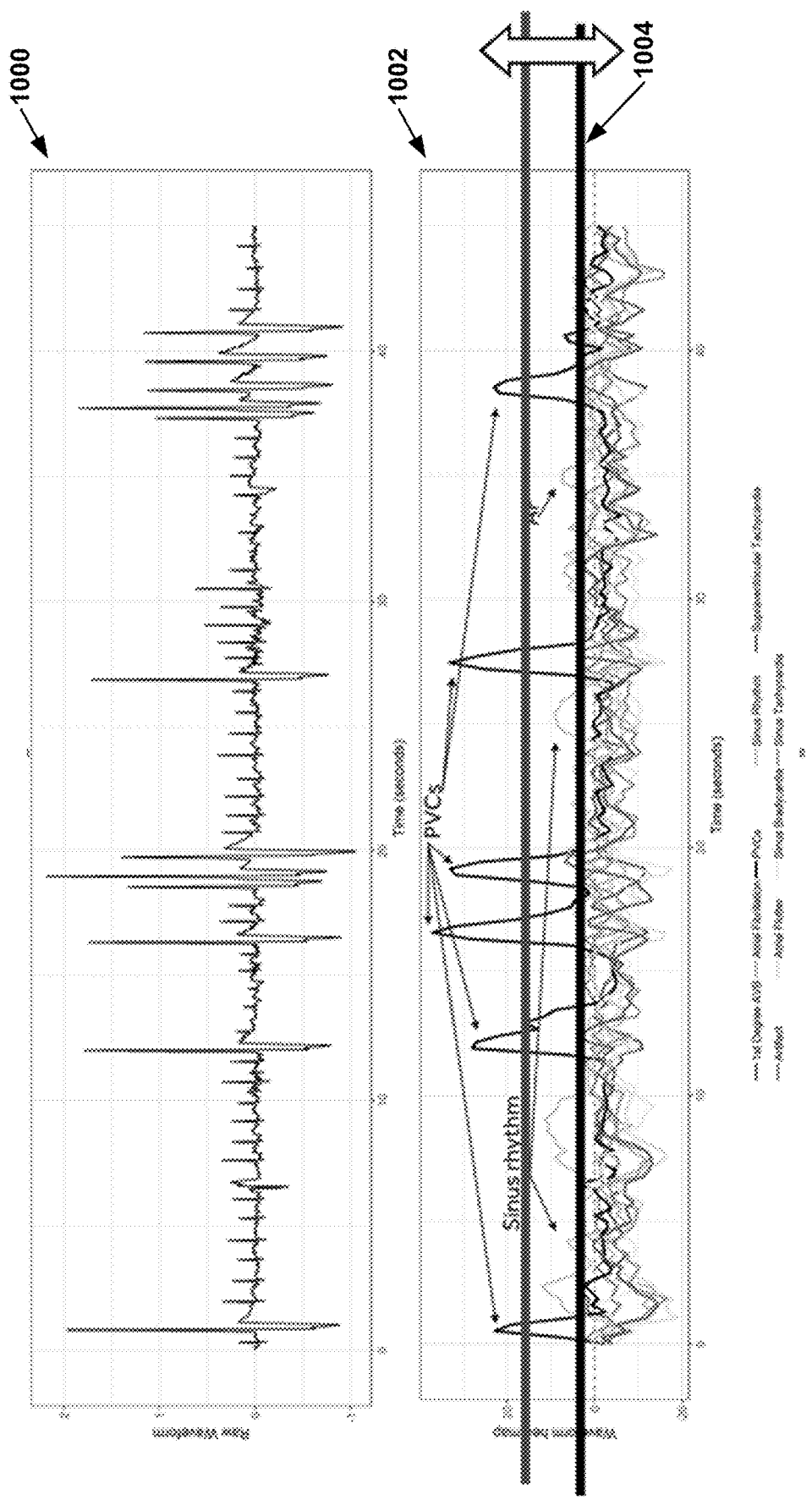
FIG. 10 is a conceptual diagram that includes an example graph of a raw cardiac electrical waveform during a time period and an example graph of probabilities of occurrences of cardiac arrhythmias during the same time period, in accordance with techniques of this disclosure.

FIG. 10 is a conceptual diagram that includes an example graph 1000 of a raw cardiac electrical waveform during a time period and an example graph 1002 of probabilities of cardiac arrhythmia events during the same time period, in accordance with techniques of this disclosure. In the example of FIG. 10, graph 1000 corresponds to a cardiac electrogram (EGM) that indicates an overall magnitude of the heart's electrical potential as recorded over the time period. In the example of FIG. 10, the time period is approximately 45 seconds in duration.

Graph 1002 includes waveforms corresponding to different cardiac arrhythmias in a set of cardiac arrhythmias. For instance, graph 1002 may include waveforms corresponding to different ICD-10 types). In some examples, the set of cardiac arrhythmias may be selected based on physician interest or patient condition.

In the example of FIG. 10, the set of cardiac arrhythmias includes $1^{st}$ degree atrioventricular block (AVB), atrial fibrillation, premature ventricular contractions (PVCs), sinus rhythm, supraventricular tachycardia, noise/non-physiological signal segments (labeled, "artifact" in FIG. 10), atrial flutter, sinus bradycardia, and sinus tachycardia. For each of the cardiac arrhythmias, the waveform corresponding to the cardiac arrhythmia is based on sample probability values that indicate probabilities that an occurrences of the cardiac arrhythmia occurred during temporal windows ending at time values corresponding to the sample probability values. The waveforms shown in the example of FIG. 10 are determined based on the waveform of graph 1000. In the example of FIG. 10, probability values are mapped (e.g., linearly scaled) to index values for ease of interpretation. In the example of FIG. 10, the index values are labeled as "waveform heatmap" values.

In the example of FIG. 10, a threshold bar 1004 is superimposed on graph 1002. Threshold bar 1004 is positioned at a location on graph 1002 that corresponds to a desired probability threshold for patient 14. In the example of FIG. 10, threshold bar 1004 is positioned at a location on graph 1002 that corresponds to an index value of 2. If the probability value of one of the cardiac arrhythmias rises above the probability threshold corresponding to the position indicated by threshold bar 1004, computing system 24 may generate a notification indicating that patient 14 is likely to have experienced an occurrence of the cardiac arrhythmia. For instance, in the example of FIG. 10, given the position of threshold bar 1004, computing system 24 may determine that the patient is likely to have experienced six occurrences of PVC, two or more occurrences of a sinus rhythm arrhythmia, and an occurrence of atrial fibrillation.

As shown in the example of FIG. 10, computing system 24 may receive an indication of user input to update the position of threshold bar 1004 to a higher position in graph 1002. Thus, given the updated position of threshold bar 1004, computing system 24 may still determine that patient 14 is likely to have experienced six occurrences of PVC, but does not determine that patient 14 has experienced an occurrence of the sinus rhythm arrhythmia or the occurrence of atrial fibrillation.

In some examples, there may be different threshold bars for different cardiac arrhythmias. For instance, there may be a first threshold bar for $1^{st}$ degree AVC, a second threshold bar for atrial fibrillation, a third threshold bar for PVCs, and so on. Thus, a user may be able to set different probability thresholds for patient 14 for different cardiac arrhythmias. For instance, the user may require a high probability threshold for atrial flutter if patient 14 is known to frequently experience atrial flutter without serious effects but may require a lower probability threshold for sinus bradycardia.

In some examples, the techniques of the disclosure include a system that comprises means to perform any method described herein. In some examples, the techniques of the disclosure include a computer-readable medium comprising instructions that cause processing circuitry to perform any method described herein.

The following is a non-limiting list of examples that are in accordance within one or more techniques of this disclosure.

Example 1. A method comprising: generating, by a computing system that comprises processing circuitry and a storage medium, a set of sample probability values by applying a machine learning model to a sample set of patient data, wherein: the machine learning model is trained using patient data for a plurality of patients, the sample set comprises a plurality of temporal windows, and for each respective temporal window of the plurality of temporal windows, the machine learning model is configured to determine a respective probability value in the set of sample probability values that indicates a probability that a cardiac arrhythmia occurred during the respective temporal window; generating, by the computing system, graphical data based on the sample probability values; outputting, by the computing system, a user interface for display on a display device, the user interface comprising the graphical data; receiving, by the computing system, via the user interface, an indication of user input to select a probability threshold for a patient; receiving, by the computing system, patient data for the patient, wherein the patient data is collected by one or more medical devices; applying, by the computing system, the machine learning model to the patient data to determine a current probability value that indicates a probability that the patient has experienced an occurrence of a cardiac arrhythmia; determining, by the computing system, that the current probability value exceeds the probability threshold for the patient; and in response to determining that the current probability value is greater than or equal to the probability threshold for the patient, generating, by the computing system, a notification indicating that the patient has likely experienced the occurrence of the cardiac arrhythmia.

Example 2. The method of example 1, wherein: generating the graphical data comprises generating, by the computing system, a receiver operating curve (ROC), wherein generating the ROC comprises: for each evaluation probability threshold of a plurality of evaluation probability thresholds: determining, by the computing system, a sensitivity value for the respective evaluation probability threshold as a ratio of: (i) a total number of sample probability values in the set of sample probability values that are greater than or equal to the respective evaluation probability threshold to (ii) a total number of the temporal windows in the sample set that actually contain occurrences of the cardiac arrhythmia that actually occurred in the sample set; determining, by the computing system, a specificity value for the respective probability value as a ratio of: (i) a total number of the sample probability values that are not greater than or equal to the respective evaluation probability threshold to (ii) a total number of the temporal windows in the sample set that do not actually contain occurrences of the cardiac arrhythmia; and determining, by the computing system, a point on the ROC that corresponds to the respective probability value, wherein the point on the ROC that corresponds to the respective probability value is based on the sensitivity value for the respective evaluation probability threshold and the specificity value for the respective evaluation probability threshold; and receiving the indication of user input to select the probability threshold for the patient comprises: receiving, by the computing system, an indication of user input to select a point on the ROC that corresponds to the probability threshold for the patient.

Example 3. The method of any of examples 1 or 2, wherein: generating the graphical data comprises: generating, by the computing system, a graph that maps the sample probability values against time; and generating, by the computing system, a threshold indicator; and receiving the indication of user input comprises receiving, by the computing system, an indication of user input to position the threshold indicator at a location in the graph corresponding to the probability threshold for the patient.

Example 4. The method of example 3, wherein the threshold indicator comprises a threshold bar superimposed on the graph and oriented parallel to a time axis of the graph.

Example 5. The method of any of examples 1-4, wherein receiving the patient data for the patient comprises receiving, by the computing system, cardiac electrical waveform data for the patient.

Example 6. The method of any of examples 1-5, further comprising receiving, by the computing system, an indication of user input to update the probability threshold for the patient.

Example 7. The method of any of examples 1-6, wherein the medical device comprises a wearable medical device or an implantable medical device (IMD).

Example 8. The method of any of examples 1-7, wherein: the cardiac arrhythmia is a first cardiac arrhythmia in a plurality of cardiac arrhythmias, and the method comprises, for each respective cardiac arrhythmia of the plurality of cardiac arrhythmias: generating, by the computing system, a respective set of sample probability values by applying a respective machine learning model to a respective sample set of patient data, wherein: the respective machine learning model is trained using patient data for the plurality of patients, the respective sample set comprises a respective plurality of temporal windows, and for each respective temporal window of the respective plurality of temporal windows, the respective machine learning model is configured to determine a respective probability value in the respective set of sample probability values that indicates a probability that the respective cardiac arrhythmia occurred during the respective temporal window; generating, by the computing system, respective graphical data based on the respective set of sample probability values; outputting, by the computing system, the user interface for display on the display device such that the user interface comprises the respective graphical data; receiving, by the computing system, via the user interface, an indication of user input to select a respective probability threshold for the patient; applying, by the computing system, the machine learning model to the patient data to determine a respective probability value that indicates a probability that the patient has experienced an occurrence of the respective cardiac arrhythmia; determining, by the computing system, that the respective probability value exceeds the respective probability threshold; and in response to determining that the respective probability value is greater than or equal to the respective probability threshold, generating, by the computing system, a notification indicating that the patient has likely experienced the occurrence of the respective cardiac arrhythmia.

Example 9. The method of any of examples 1-8, further comprising presenting, by the computing system, data indicating the anticipated review burden versus the anticipated diagnostic yield for the probability threshold for the patient.

Example 10. A computing system comprising processing circuitry and a storage medium, the computing device configured to perform the methods of any of examples 1-9.

Example 11. A method as described in the specification.

It should be understood that various aspects and examples disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:
    generating, by a computing system that comprises processing circuitry and one or more storage media, a set of sample probability values by applying a machine learning model to a sample set of patient data, wherein:
        the machine learning model is trained using patient data for a plurality of patients,
        the sample set comprises a plurality of temporal windows, and
        for each respective temporal window of the plurality of temporal windows, the machine learning model is configured to determine a respective probability value in the set of sample probability values that indicates a probability that a cardiac arrhythmia occurred during the respective temporal window;
    generating, by the computing system, graphical data based on the sample probability values;
    outputting, by the computing system, a user interface for display on a display device, the user interface comprising the graphical data;
    receiving, by the computing system, via the user interface, an indication of user input to select a probability threshold for a patient;
    receiving, by the computing system, patient data for the patient, wherein the patient data for the patient is collected by one or more medical devices;
    applying, by the computing system, the machine learning model to the patient data for the patient to determine a current probability value that indicates a probability that the patient has experienced an occurrence of the cardiac arrhythmia;
    determining, by the computing system, that the current probability value exceeds the probability threshold for the patient;
    in response to determining that the current probability value is greater than or equal to the probability threshold for the patient, generating, by the computing system, a notification indicating that the patient has likely experienced the occurrence of the cardiac arrhythmia; and
    presenting, by the computing system, data indicating an anticipated review burden versus an anticipated diagnostic yield for the probability threshold for the patient.

2. The method of claim 1, wherein:
    generating the graphical data comprises generating, by the computing system, a receiver operating curve (ROC), wherein generating the ROC comprises:
        for each evaluation probability threshold of a plurality of evaluation probability thresholds:
            determining, by the computing system, a sensitivity value for the respective evaluation probability threshold as a ratio of: (i) a total number of sample probability values in the set of sample probability values that are greater than or equal to the respective evaluation probability threshold to (ii) a total number of the temporal windows in the sample set that actually contain occurrences of the cardiac arrhythmia that actually occurred in the sample set;
            determining, by the computing system, a specificity value for the respective probability value as a ratio of: (i) a total number of the sample probability values that are not greater than or equal to the respective evaluation probability threshold to (ii) a total number of the temporal windows in the sample set that do not actually contain occurrences of the cardiac arrhythmia; and
            determining, by the computing system, a point on the ROC that corresponds to the respective probability value, wherein the point on the ROC that corresponds to the respective probability value is based on the sensitivity value for the respective evaluation probability threshold and the specificity value for the respective evaluation probability threshold; and
    receiving the indication of user input to select the probability threshold for the patient comprises: receiving, by the computing system, an indication of user input to select a point on the ROC that corresponds to the probability threshold for the patient.

3. The method of claim 1, wherein:
    generating the graphical data comprises:
        generating, by the computing system, a graph that maps the sample probability values against time; and
        generating, by the computing system, a threshold indicator; and
    receiving the indication of user input comprises receiving, by the computing system, an indication of user input to position the threshold indicator at a location in the graph corresponding to the probability threshold for the patient.

4. The method of claim 3, wherein the threshold indicator comprises a threshold bar superimposed on the graph and oriented parallel to a time axis of the graph.

5. The method of claim 1, wherein receiving the patient data for the patient comprises receiving, by the computing system, cardiac electrical waveform data for the patient.

6. The method of claim 1, further comprising receiving, by the computing system, an indication of user input to update the probability threshold for the patient.

7. The method of claim 1, wherein the medical devices include a wearable medical device or an implantable medical device (IMD).

8. The method of claim 1, wherein:
    the cardiac arrhythmia is a first cardiac arrhythmia in a plurality of cardiac arrhythmias, and
    the method comprises, for each respective cardiac arrhythmia of the plurality of cardiac arrhythmias:

generating, by the computing system, a respective set of sample probability values by applying a respective machine learning model to a respective sample set of patient data, wherein:
  the respective machine learning model is trained using patient data for the plurality of patients,
  the respective sample set comprises a respective plurality of temporal windows, and
  for each respective temporal window of the respective plurality of temporal windows, the respective machine learning model is configured to determine a respective probability value in the respective set of sample probability values that indicates a probability that the respective cardiac arrhythmia occurred during the respective temporal window;
generating, by the computing system, respective graphical data based on the respective set of sample probability values;
outputting, by the computing system, the user interface for display on the display device such that the user interface comprises the respective graphical data;
receiving, by the computing system, via the user interface, an indication of user input to select a respective probability threshold for the patient;
applying, by the computing system, the machine learning model to the patient data to determine a respective probability value that indicates a probability that the patient has experienced an occurrence of the respective cardiac arrhythmia;
determining, by the computing system, that the respective probability value exceeds the respective probability threshold; and
in response to determining that the respective probability value is greater than or equal to the respective probability threshold, generating, by the computing system, a notification indicating that the patient has likely experienced the occurrence of the respective cardiac arrhythmia.

9. The method of claim 1, wherein the patient is a first patient, the patient data for the patient is first patient data, the current probability value is a first current probability value, and the one or more medical devices are one or more first medical devices, and the method further comprises:
receiving, by the computing system, second patient data for a second patient, wherein the second patient data is collected by one or more second medical devices;
applying, by the computing system, the machine learning model to the second patient data to determine a second current probability value that indicates a probability that the second patient has experienced an occurrence of the cardiac arrhythmia;
determining, by the computing system, that the second current probability value exceeds a default probability threshold, wherein the default probability threshold is set to maximize diagnostic yield; and
in response to determining that the second current probability value is greater than or equal to the default probability threshold, generating, by the computing system, a second notification indicating that the second patient has likely experienced the occurrence of the cardiac arrhythmia.

10. A computing system comprising:
one or more processing circuits; and
one or more storage media storing instructions that, when executed by the one or more processing circuits, cause the one or more processing circuits to:
  generate a set of sample probability values by applying a machine learning model to a sample set of patient data, wherein:
    the machine learning model is trained using patient data for a plurality of patients,
    the sample set comprises a plurality of temporal windows, and
    for each respective temporal window of the plurality of temporal windows, the machine learning model is configured to determine a respective probability value in the set of sample probability values that indicates a probability that a cardiac arrhythmia occurred during the respective temporal window;
  generate graphical data based on the sample probability values;
  output a user interface for display on a display device, the user interface comprising the graphical data;
  receive, via the user interface, an indication of user input to select a probability threshold for a patient;
  receive patient data for the patient, wherein the patient data for the patient is collected by one or more medical devices;
  apply the machine learning model to the patient data for the patient to determine a current probability value that indicates a probability that the patient has experienced an occurrence of the cardiac arrhythmia;
  determine that the current probability value exceeds the probability threshold for the patient;
  in response to determining that the current probability value is greater than or equal to the probability threshold for the patient, generate a notification indicating that the patient has likely experienced the occurrence of the cardiac arrhythmia; and
  present data indicating an anticipated review burden versus an anticipated diagnostic yield for the probability threshold for the patient.

11. The computing system of claim 10, wherein:
the one or more processing circuits are configured such that, as part of generating the graphical data, the one or more processing circuits generate a receiver operating curve (ROC), wherein, the one or more processing circuits are configured such that, as part of generating the ROC, the one or more processing circuits:
for each evaluation probability threshold of a plurality of evaluation probability thresholds:
  determine a sensitivity value for the respective evaluation probability threshold as a ratio of: (i) a total number of sample probability values in the set of sample probability values that are greater than or equal to the respective evaluation probability threshold to (ii) a total number of the temporal windows in the sample set that actually contain occurrences of the cardiac arrhythmia that actually occurred in the sample set;
  determine a specificity value for the respective probability value as a ratio of: (i) a total number of the sample probability values that are not greater than or equal to the respective evaluation probability threshold to (ii) a total number of the temporal windows in the sample set that do not actually contain occurrences of the cardiac arrhythmia; and
  determine a point on the ROC that corresponds to the respective probability value, wherein the point on the ROC that corresponds to the respective probability value is based on the sensitivity value for the respective evaluation probability threshold and the specificity value for the respective evaluation probability threshold; and the one or more processing circuits are configured such that, as part of receiving the indication of user input to select the probability threshold for the patient, the one or more processing circuits receive an indication of user input to select a point on the ROC that corresponds to the probability threshold for the patient.

12. The computing system of claim 10, wherein:
the one or more processing circuits are configured such that, as part of generating the graphical data, the one or more processing circuits:
generate a graph that maps the sample probability values against time; and
generate a threshold indicator; and
the one or more processing circuits are configured such that, as part of receiving the indication of user input, the one or more processing circuits receive an indication of user input to position the threshold indicator at a location in the graph corresponding to the probability threshold for the patient.

13. The computing system of claim 12, wherein the threshold indicator comprises a threshold bar superimposed on the graph and oriented parallel to a time axis of the graph.

14. The computing system of claim 10, wherein the one or more processing circuits are configured such that, as part of receiving the patient data for the patient, the one or more processing circuits are configured to receive cardiac electrical waveform data for the patient.

15. The computing system of claim 10, wherein the one or more processing circuits are further configured to receive an indication of user input to update the probability threshold for the patient.

16. The computing system of claim 10, wherein the one or more medical devices comprises a wearable medical device or an implantable medical device (IMD).

17. The computing system of claim 10, wherein:
the cardiac arrhythmia is a first cardiac arrhythmia in a plurality of cardiac arrhythmias, and
the one or more processing circuits are configured to, for each respective cardiac arrhythmia of the plurality of cardiac arrhythmias:
generating, by the computing system, a respective set of sample probability values by applying a respective machine learning model to a respective sample set of patient data, wherein:
the respective machine learning model is trained using patient data for the plurality of patients,
the respective sample set comprises a respective plurality of temporal windows, and
for each respective temporal window of the respective plurality of temporal windows, the respective machine learning model is configured to determine a respective probability value in the respective set of sample probability values that indicates a probability that the respective cardiac arrhythmia occurred during the respective temporal window;
generating, by the computing system, respective graphical data based on the respective set of sample probability values;
outputting, by the computing system, the user interface for display on the display device such that the user interface comprises the respective graphical data;
receiving, by the computing system, via the user interface, an indication of user input to select a respective probability threshold for the patient;
applying, by the computing system, the machine learning model to the patient data for the patient to determine a respective probability value that indicates a probability that the patient has experienced an occurrence of the respective cardiac arrhythmia;
determining, by the computing system, that the respective probability value exceeds the respective probability threshold; and
in response to determining that the respective probability value is greater than or equal to the respective probability threshold, generating, by the computing system, a notification indicating that the patient has likely experienced the occurrence of the respective cardiac arrhythmia.

18. One or more non-transitory computer-readable data storage media having instructions stored thereon that, when executed by one or more processing circuit of a computing system, cause the one or more processing circuits to:
generate a set of sample probability values by applying a machine learning model to a sample set of patient data, wherein:
the machine learning model is trained using patient data for a plurality of patients,
the sample set comprises a plurality of temporal windows, and
for each respective temporal window of the plurality of temporal windows, the machine learning model is configured to determine a respective probability value in the set of sample probability values that indicates a probability that a cardiac arrhythmia occurred during the respective temporal window;
generate graphical data based on the sample probability values;
output a user interface for display on a display device, the user interface comprising the graphical data;
receive, via the user interface, an indication of user input to select a probability threshold for a patient;
receive patient data for the patient, wherein the patient data for the patient is collected by one or more medical devices;
apply the machine learning model to the patient data for the patient to determine a current probability value that indicates a probability that the patient has experienced an occurrence of the cardiac arrhythmia;
determine that the current probability value exceeds the probability threshold for the patient;
in response to determining that the current probability value is greater than or equal to the probability threshold for the patient, generate a notification indicating that the patient has likely experienced the occurrence of the cardiac arrhythmia; and
present data indicating an anticipated review burden versus an anticipated diagnostic yield for the probability threshold for the patient.

* * * * *